(12) United States Patent
Kwon et al.

(10) Patent No.: US 10,406,188 B1
(45) Date of Patent: Sep. 10, 2019

(54) METHOD FOR INHIBITING TELOMERASE IN CANCER CELL USING LUTERION

(71) Applicant: LUTERION CO., LTD., Gyeonggi-do (KR)

(72) Inventors: Young Ah Kwon, Seoul (KR); Won Cheol Choi, Incheon (KR); Suk Hoon Choi, Seoul (KR); Chang Hoon Choi, Seoul (KR)

(73) Assignee: LUTERION CO., LTD., Gyeonggi-Do (KR)

(*) Notice: Subject to any disclaimer, the term of this patent is extended or adjusted under 35 U.S.C. 154(b) by 0 days.

(21) Appl. No.: 15/641,947

(22) Filed: Jul. 5, 2017

Related U.S. Application Data

(63) Continuation-in-part of application No. PCT/KR2016/000067, filed on Jan. 5, 2016.

(30) Foreign Application Priority Data

Jan. 5, 2015 (KR) .................. 10-2015-0000751

(51) Int. Cl.
*C12N 5/04* (2006.01)
*A61K 36/22* (2006.01)

(52) U.S. Cl.
CPC .................................. *A61K 36/22* (2013.01)

(58) Field of Classification Search
None
See application file for complete search history.

(56) References Cited

U.S. PATENT DOCUMENTS

| | | | |
|---|---|---|---|
| 5,583,016 A | 12/1996 | Villeponteau et al. | |
| 5,656,638 A | 8/1997 | Gaeta et al. | |
| 5,760,062 A | 6/1998 | Gaeta et al. | |
| 5,767,278 A | 6/1998 | Gaeta et al. | |
| 5,770,613 A | 6/1998 | Gaeta et al. | |
| 5,863,936 A | 1/1999 | Gaeta et al. | |
| 6,261,836 B1 | 7/2001 | Cech et al. | |
| 6,444,650 B1 | 9/2002 | Cech et al. | |
| 6,548,298 B2 | 4/2003 | Villeponteau et al. | |
| 2012/0283322 A1 | 11/2012 | Park et al. | |
| 2016/0169870 A1* | 6/2016 | Kwon | C12N 5/00 435/29 |
| 2016/0324896 A1* | 11/2016 | Choi | A61K 35/12 |
| 2016/0334389 A1* | 11/2016 | Choi | G01N 33/5026 |
| 2017/0361243 A1* | 12/2017 | Kwon | B03C 1/32 |
| 2018/0051252 A1* | 2/2018 | Choi | C12N 5/0634 |

FOREIGN PATENT DOCUMENTS

| | | |
|---|---|---|
| JP | 55-111422 A | 8/1980 |
| JP | 2003061615 A | 3/2003 |
| JP | 2009513624 A | 4/2009 |
| JP | 2013-535500 A | 9/2013 |
| KR | 10-2006-0132802 A | 12/2006 |
| KR | 10-2008-0041169 A | 5/2008 |
| KR | 10-2011-0099538 A | 9/2011 |
| KR | 10-2016-0084820 A | 7/2016 |
| KR | 10-2016-0114022 A | 10/2016 |
| KR | 10-2016-0115886 A | 10/2016 |
| WO | WO2007049846 A1 | 5/2007 |
| WO | 2012053976 A1 | 4/2012 |
| WO | 2014028763 A1 | 2/2014 |
| WO | 2015005553 A1 | 1/2015 |
| WO | WO2015108342 A1 | 7/2015 |
| WO | WO2016111552 A1 | 7/2016 |

OTHER PUBLICATIONS

Kim, J.H., et al., "Integrating Traditional Medicine into Modern Inflammatory Diseases Care: Multitargeting by Rhus Verniciflua Stokes", "Mediators of Inflammation", 2014, pp. 1-17.
Lee, S., et al., "Shrinkage of Gastric Cancer in an Elderly Patient Who Received Rhus Verniciflua Stokes Extract", "The Journal of Alternative and Complementary Medicine", 2010, pp. 497-500, vol. 16, No. 4.
Lee, S., et al., "Efficacy and Safety of Standardized Allergen-Removed Rhus Verniciflua Stokes Extract in Patients with Advanced or Metastatic Pancreatic Cancer: A Korean Single-Center Experience", "Oncology", 2011, pp. 312-318.
Artandi, S. E., et al., "Mice without telomerase: what can they teach us about human cancer?", "Nature Medicine", Aug. 2000, pp. 852-855, vol. 6, No. 8.
Blackburn, E. H., "Telomerases", "Annual Review of Biochemistry", 1992, pp. 113-129, vol. 61.
Bryan, T. M. et al., "Telomere elongation in immortal human cells without detectable telomerase activity", "The EMBO Journal", 1995, pp. 4240-4248, vol. 14, No. 17.
Bryan, T. M., et al., "Telomerase and the maintenance of chromosome ends", "Current Opinion in Cell Biology", 1999, pp. 318-324, vol. 11.
Burchett, K. M., et al., "Telomerase Inhibitor Imetelstat (GRN163L) Limits the Lifespan of Human Pancreatic Cancer Cells", "PLOS One", Jan. 7, 2014, p. e85155, vol. 9, No. 1.
Burger, A. M., et al., "Inhibition of Telomerase Activity by Cisplatin in Human Testicular Cancer Cells", "European Journal of Cancer", 1997, pp. 638-644, vol. 33, No. 4.

(Continued)

*Primary Examiner* — Ralph J Gitomer
(74) *Attorney, Agent, or Firm* — Hultquist, PLLC; Steven J. Hultquist

(57) ABSTRACT

The present disclosure relates to a method for inhibiting telomerase in cancer cells by means of luterion and, more particularly, to a method for inhibiting telomerase activity in cancer tissues, cancer cells or a cancer patient, the method in which administered are: an anti-cancer composition comprising luterion; a composition for inhibiting telomerase activity in cancer cells; and luterion. Luterion, according to the present disclosure, has the advantage of effectively inhibiting only the proliferation of cancer cells, without affecting normal cells, by inhibiting telomerase activity in cancer cells.

7 Claims, 21 Drawing Sheets
(18 of 21 Drawing Sheet(s) Filed in Color)

(56) References Cited

OTHER PUBLICATIONS

Chadeneau, C., et al., "Telomerase Activity Associated with Acquisition of Malignancy in Human Colorectal Cancer", "Cancer Research", Jun. 15, 1995, pp. 2533-2536, vol. 55.

Counter, C. M.. et al., "Telomere shortening associated with chromosome instability is arrested in immortal cells which express telomerase activity", "The EMBO Journal", 1992, pp. 1921-1929, vol. 11, No. 5.

Counter, C. M., et al., "Telomerase activity in human ovarian carcinoma", "Proceedings of the National Academy of Sciences", Apr. 1994, pp. 2900-2904, vol. 91.

Gowan, S. M., et al., "Potent Inhibition of Telomerase by Small-Molecule Pentacyclic Acridines Capable of Interacting with G-Quadruplexes", "Molecular Pharmacology", 2001, pp. 981-988, vol. 60, No. 5.

Gowan, S. M., et al., "A G-Quadruplex-Interactive Potent Small-Molecule Inhibitor of Telomerase Exhibiting in Vitro and in Vivo Antitumor Activity", "Molecular Pharmacology", 2002, pp. 1154-1162, vol. 61, No. 5.

Hahn, W. C., et al., "Inhibition of telomerase limits the growth of human cancer cells", "Nature Medicine", Oct. 1999, pp. 1164-1170, vol. 5, No. 10.

Hiyama, E., et al., "Correlating telomerase activity levels with human neuroblastoma outcomes", "Nature Medicine", Mar. 1995, pp. 249-255, vol. 1, No. 3.

Izbicka, E., et al., "Effects of Cationic Porphyrins as G-Quadruplex Interactive Agents in Human Tumor Cells", "Cancer Research", Feb. 1, 1999, pp. 639-644, vol. 59.

Kondo, Y., et al., "Treatment of prostate cancer in vitro and in vivo with 2-5A-anti-telomerase RNA component", "Oncogene", 2000, pp. 2205-2211, vol. 19.

Norton, J. C., et al., "Inhibition of human telomerase activity by peptide nucleic acids", "Nature Biotechnology", May 1996, pp. 615-619, vol. 14.

Perry, P. J., et al., "2,7-Disubstituted Amidofluorenone Derivatives as Inhibitors of Human Telomerase", "Journal of Medicinal Chemistry", Jun. 17, 1999, pp. 2679-2684, vol. 42, No. 14.

Pitts, A. E., et al., "Inhibition of human telomerase by 2'-O-methyl-RNA", "Proceedings of the National Academy of Sciences", Sep. 1998, pp. 11549-11554, vol. 95.

Shay, J. W., et al., "Spontaneous In Vitro Immortalization of Breast Epithelial Cells from a Patient with Li-Fraumeni Syndrome", "Molecular and Cellular Biology", Jan. 1995, pp. 425-432, vol. 15, No. 1.

Strahl, C., et al., "Effects of Reverse Transcriptase Inhibitors on Telomere Length and Telomerase Activity in Two Immortalized Human Cell Lines", "Molecular and Cellular Biology", Jan. 1996, pp. 53-65, vol. 16, No. 1.

Tickner, J. A., et al., "Functions and therapeutic roles of exosomes in cancer", "Frontiers in Oncology", May 27, 2014, pp. 1-8, vol. 4, No. 127.

Yokoyama, Y., et al., "Attenuation of Telomerase Activity by a Hammerhead Ribozyme Targeting the Template Region of Telomerase RNA in Endometrial Carcinoma Cells", "Cancer Research", Dec. 1, 1998, pp. 5406-5410, vol. 58.

Zhang, X., et al., "Telomere shortening and apoptosis in telomerase-inhibited human tumor cells", "Genes & Development", 1999, pp. 2388-2399, vol. 13.

Note: For the non-patent literature citations that no month of publication is indicated, the year of publication is more than 1 year prior to the effective filing date of the present application.

\* cited by examiner

METHOD FOR INHIBITING TELOMERASE IN CANCER CELL USING LUTERION

CROSS-REFERENCE TO RELATED APPLICATIONS

This is a continuation-in-part application under 35 U.S.C. § 120 of International Patent Application No. PCT/KR2016/000067 filed Jan. 5, 2016, which in turn claims priority of Korean Patent Application No. 10-2015-0000751 filed Jan. 5, 2015. The disclosures of such international patent application and Korean priority patent application are hereby incorporated herein by reference in their respective entireties, for all purposes.

BACKGROUND

Field

The present disclosure relates to a method for inhibiting telomerase in cancer cells using luterion, and more particularly, to a method for inhibiting telomerase activity in cancer tissues, cancer cells or a cancer patient, the method in which administered are: an anti-cancer composition comprising the luterion; a composition for inhibiting telomerase activity in cancer cells; and the luterion.

Description of the Related Art

Telomerase is a ribonucleoprotein that catalyzes the addition of telomere repeat sequence to the chromosome terminal (Blackburn, *Ann. Rev. Biochem.*, 61:113-129, 1992). Telomerase activity is not found in normal cells except for specific cells such as hemapoietic stem cells, whereas high telomerase activity is observed in most cancer cells. Detection and quantification of telomerase activity is critical to the diagnosis of cancers since telomerase is believed to be involved in maintaining an infinite proliferation of cancer cells. Furthermore, inhibitors of telomerase activity are expected as anticancer agents with little side effects on normal cells (Counter C. M. et al., *EMBO J.*, 11:1921-1929, 1989; Counter C. M. et al., *Proc. Natl. Acad. Sci. USA*, 91:2900-2904, 1994; Chadeneau C. et al., *Cancer Res.*, 55:2533-2536, 1995; Hiyama et al., *Nature Med.*, 1:249-255, 1995; Shay J. W. et al., *Mol. Cell. Biol.*, 15:425-432, 1995).

Human telomerase has been cloned with genes encoding protein and RNA, and many studies are under way to find telomerase inhibitors (U.S. Pat. Nos. 6,261,836; 5,583,016). Telomerase inhibitors so far identified include small molecule compounds and oligonucleotides. Various documents disclose that oligonucleotides and the like for suppressing the telomerase targeted to mRNA encoding the telomerase protein component (its human form is human telomerase reverse transcriptase or hTERT) or the RNA component of telomerase holoenzyme (its human form is human telomerase RNA or hTR). Oligonucleotides targeted to hTERT mRNA generally bind to mRNA to cause destruction of mRNA, thereby acting as a traditional antisense drug to prevent the production of hTERT protein (U.S. Pat. No. 6,444,650). Certain oligonucleotides targeted to hTR bind to hTR molecules present in the telomerase holoenzyme to destroy enzyme function (U.S. Pat. No. 6,548,298). hTERT (human telomerase reverse transcriptase) is one of the most important enzymes that regulate the immortality and proliferation ability of cancer cells. While such telomerase has 80% to 90% telomerase activity in infinitely cloned germ cells, hematopoietic cells, and cancer cells, but normal cells do not have such activity (Bryan, T. M. et al., *Curr. Opin. Cell Biol.*, 11:318-324, 1999). Recently, attempts have been made to inhibit the proliferation of cancer cells by developing inhibitors of telomerase that is involved in cell growth using such characteristics of telomerase (Bryan, T. M. et al, *Embo J.* 14:4240-4248, 1995; Artandi, S. E. et al., *Nat. Med.* 6:852-855, 2000).

It has been reported that an antisense strategy defined by a telomerase RNA component, such as peptide nucleic acid (Norton et al., *Nature Biotech.* 14:615-619, 1996) and phosphorothioate oligonucleotides inhibit the telomerase activity. Since telomerase is a reverse transcriptase, it has also been reported to use reverse transcriptase enzymes such as AZT, or inhibitors of other nucleosides.

There are disclosures of telomerase inhibition, if possible, due to cross-linking of the telomer repeat sequence by cisplatin (Burger et al., *Eur. J. Cancer,* 33: 638-644, 1997), a method for inhibiting the action of hTERT, which is the template RNA of the telomerase gene using antisense oligonucleotides to inhibit the telomerase activity (Pitts, A. E. et al., *Proc. Natl. Acad. Sci., USA,* 95: 11549-11554, 1998; Kondo, Y. et al., *Oncogene,* 19: 2205-2211, 2000), a method for inhibiting telomerase template RNA using hammerhead ribozyme (Yokoyama, Y. et al., *Cancer Res.,* 58: 5406-5410, 1998), inhibitors of the activity of reverse transcriptase (Strahl, C. et al., *Mol. Cell. Biol.,* 16: 53-65, 1996), expression of the dominant negative hTERT protein inhibiting normal telomerase activity (Zhang, X. et al., *Genes Dev.,* 13: 2388-2399; 1999; Hahn, W. C. et al., *Nat. Med.,* 5: 1164-1170, 1999), and small molecule inhibitors acting on stabilization of G-quadruplex inhibiting the action of telomerase by acting on the telomere structure (Perry, P. J. et al., *J. Med. Chem.,* 42:2679-2684, 1999; Gowan, S. M. et al., *Mol. Pharmacol.,* 60:981-988, 2001; Gowan, S. M. et al., *Mol. Pharmacol.,* 61:1154-1162, 2002; Izbicka, E. et al., *Cancer Res.,* 59:639-644, 1999).

Meanwhile, the present inventors observed the characteristics of the micro-substances present in the body fluids pre-discharged from patients and named the micro-materials as "luterial" and has filed Korean patent application on Jul. 12, 2013 (Korean Patent Application No. 10-2013-0082060), and furtherly has filed Korean patent application on Jan. 14, 2014 for a method for effectively isolating and culturing the above-mentioned luterial (Korean Patent Application No. 10-2014-004525). Further, "luterion," a micro-substance which is similar in a structure and function of such luterial, is present in plants and animals, and not only has RNA and/or DNA, but also blocks the growth of cancer cells to serves to restore the cells to a healthy immune system.

Therefore, the present inventors have found that, in order to apply the luterion to a pharmaceutical or food composition, it is necessary to collect a vaporizing gas generated by adding a solvent to a plant and shaking it, and then, through filtration and centrifugation, effectively remove and culture the luterion contained in the vaporizing gas, and have filed patent applicant on Jan. 6, 2015 (Korean Patent Application No. 10-2015-0001195).

Accordingly, the present inventors have made efforts to find a novel substance inhibiting telomerase, and as a result, they have found that the luterion inhibits the telomerase activity in cancer cells to inhibit the proliferation of cancer cells, thereby completing the present disclosure.

SUMMARY

An object of the present disclosure is to provide an anticancer composition which inhibits the proliferation of cancer cells through inhibition of telomerase activity.

Another object of the present disclosure is to provide a method of preventing or treating a cancer through inhibition of telomerase activity in a cancer tissue, a cancer cell, or a cancer patient.

In order to achieve the objects, the present disclosure provides a pharmaceutical composition for preventing or treating a cancer, comprising luterion as an active ingredient.

The present disclosure also provides a food composition for preventing or ameliorating a cancer comprising the luterion as an active ingredient.

The present disclosure also provides a composition for inhibiting telomerase activity of cancer cells comprising the luterion as an active ingredient.

The present disclosure also provides a method for preventing or treating a cancer, comprising administration of a composition comprising the luterion as an active ingredient.

The present disclosure also provides a method for inhibiting telomerase activity in a cancer tissue, a cancer cell, or a cancer patient, comprising administration of a composition comprising the luterion as an active ingredient.

The present disclosure also provides a method for inhibiting the proliferation of a cancer cell, comprising administration of a composition comprising the luterion as an active ingredient.

The present disclosure also provides a use of a composition comprising the luterion as an active ingredient for prevention or treatment of a cancer.

The present disclosure also provides a use of a composition comprising the luterion as an active ingredient for inhibiting telomerase activity in a cancer tissue, a cancer cell, or a cancer patient.

The present disclosure also provides a use for preparing an anticancer composition comprising the luterion as an active ingredient.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE EMBODIMENT

Unless otherwise defined, all technical and scientific terms used herein have the same meaning as commonly understood by those skilled in the art to which the present disclosure belongs. In general, the nomenclature used herein is well known and commonly used in the art.

Figure 8:
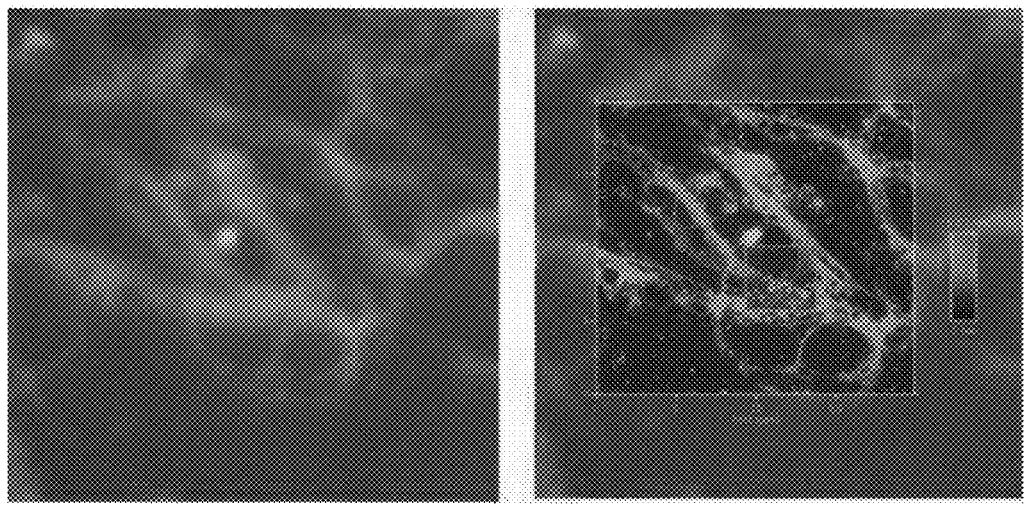
FIG. 8 is an image obtained by an atomic force microscope, showing that the luterion contains a nucleic acid therein.
Figure 9:
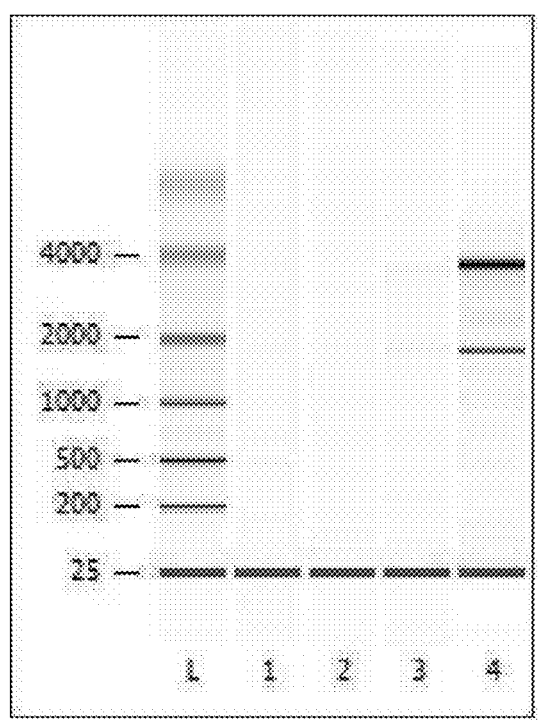
FIG. 9 is a bioanalyzer result by analyzing whether RNA is contained in the luterion (L: Control; 1:50 nm or less, 2:50 nm to 100 nm, 3:100 nm to 200 nm, 4:200 nm to 400 nm).
Figure 10:
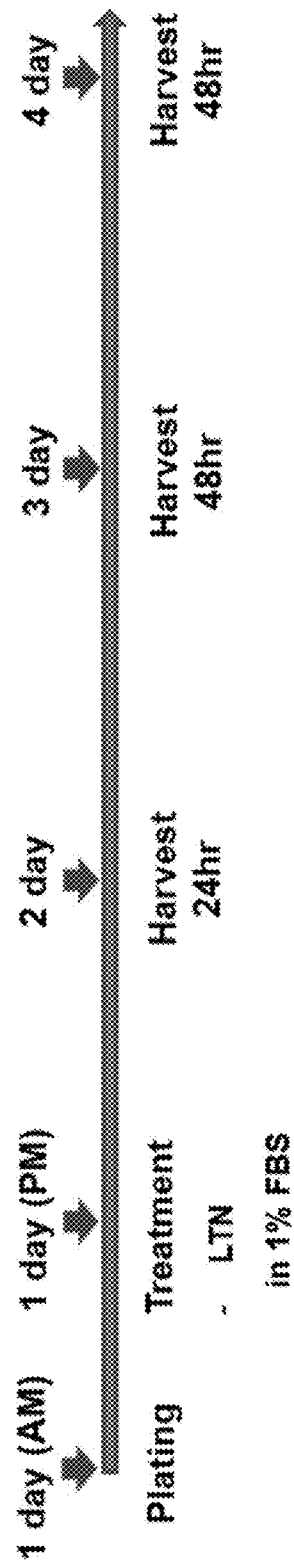
FIG. 10 is a schematic diagram illustrating a plan for measuring telomerase activity.

The terms "luterial" and "luterion" as used herein are named by the present inventors, which is a nano-sized living thing of 50 nm to 400 nm in size present in all living organisms including animals and plants, and have from virus-like size up to 800 nm to 1200 nm. Both of the luterial and luterion are distinguished from exosome or microvesicle in that they have DNA and RNA (See FIGS. 8 and 9) and have motility and adhesion. The luterial refers to a nano-sized living thing that exists in the host's body in the ecosystem. In the case of animals including humans, it may exist in blood, saliva, lymphatic fluid, semen, vaginal fluid, breast milk (especially colostrum), cord blood, brain cells, spinal cord, or bone marrow. On the other hand, the luterion refers to a nano-sized living thing whose host may be e.g., food, and can exist mainly in plants and foods.

Figure 1:
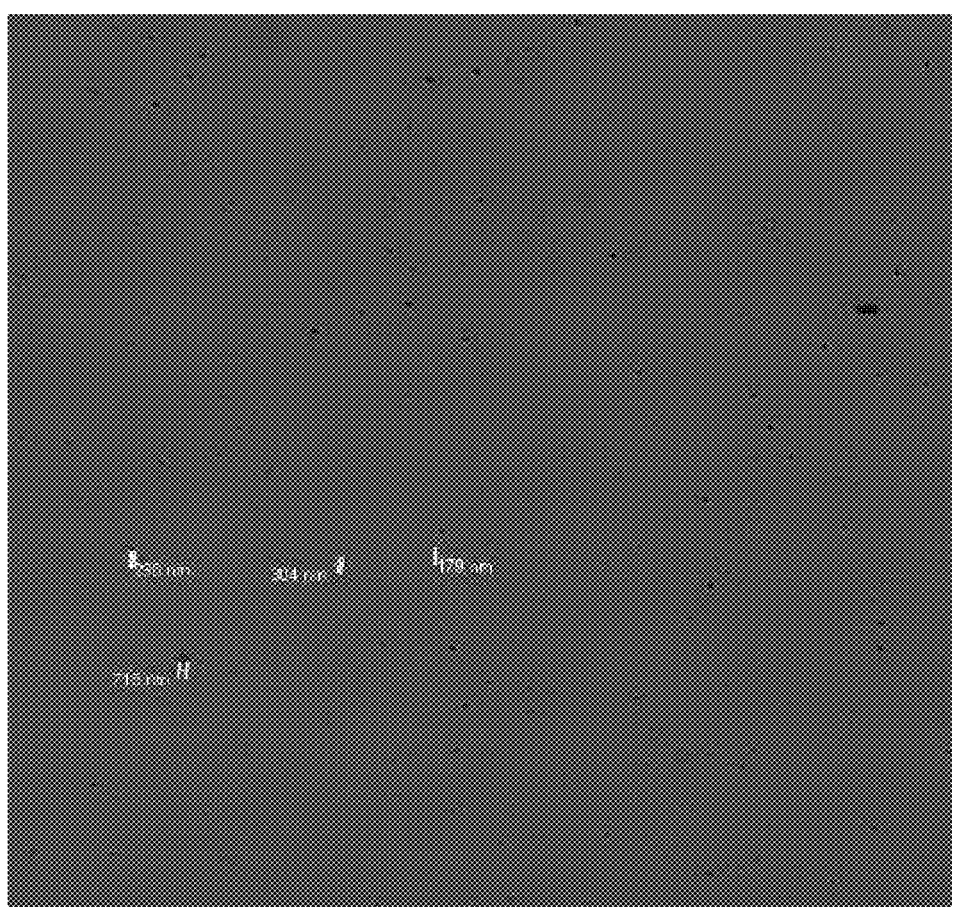
FIG. 1 is an image of the luterion taken by a confocal laser scanning microscope (Zeiss), which shows sizes thereof.
Figure 2:
FIG. 2 is an image showing the presence or absence of coloration after staining of the luterion with Mito-tracker.
Figure 3:
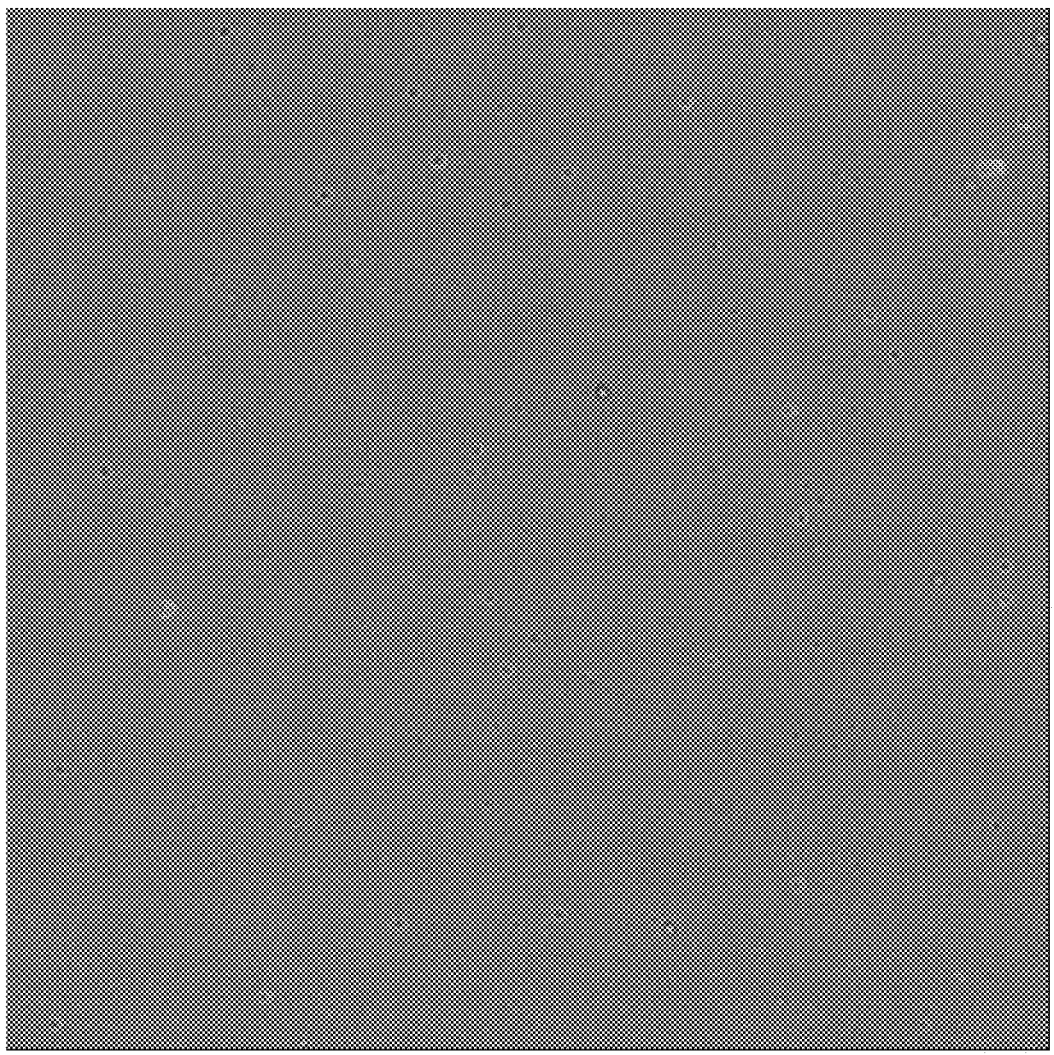
FIG. 3 is an image showing the presence or absence of coloration after staining of the luterion with Rhodamine 123.
Figure 4:
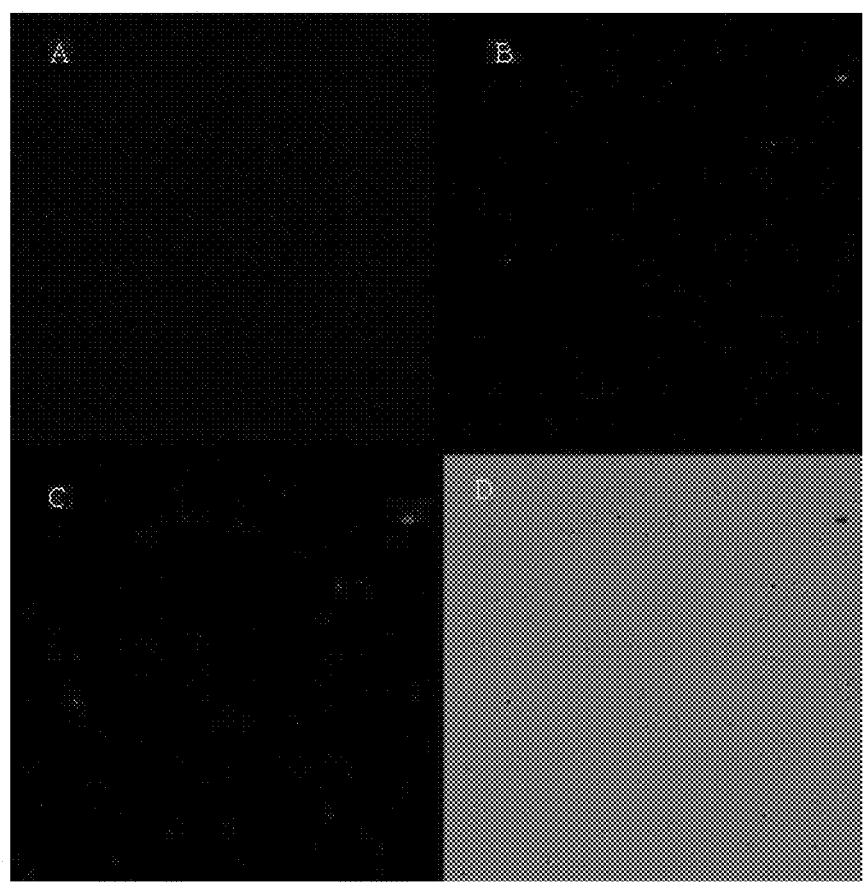
FIG. 4 illustrates comparisons of fluorescence/non-fluorescence images of the luterion (A: Janus Green B Positive, B: Rhodamine 123 Positive C: Mito-tracker Red Positive; and D: no staining).
Figure 5:
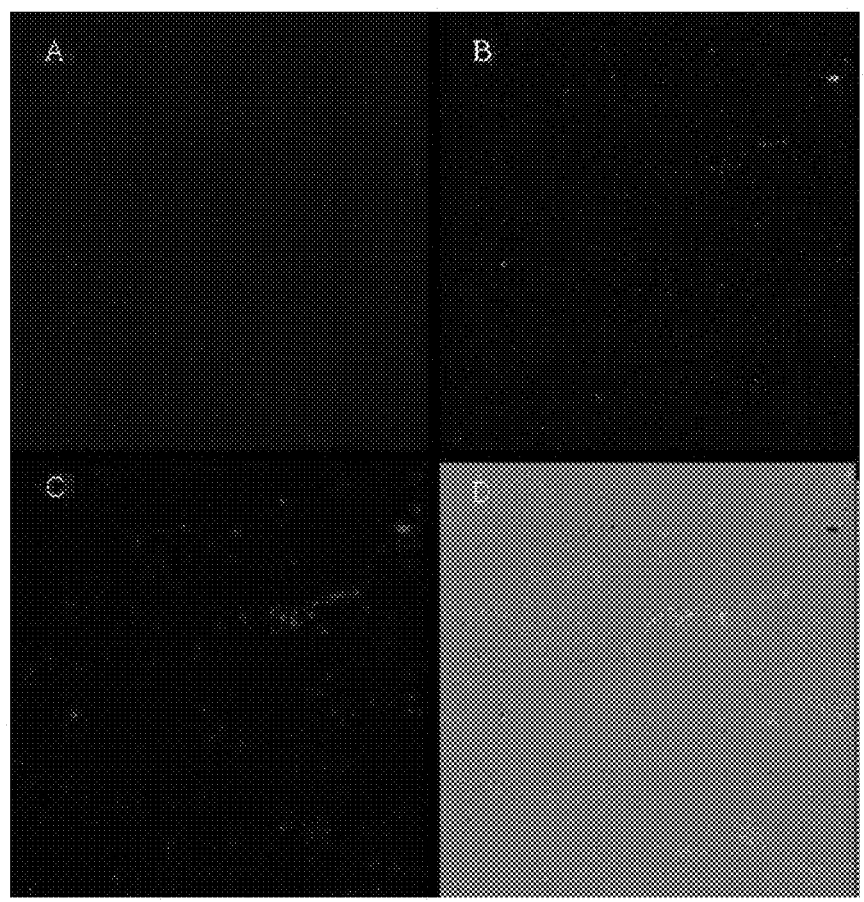
FIG. 5 illustrates whether the coloration of the luterion after commonly dyeing with Rhodamine 123, Mito tracker red, and Janus green B (A: Janus Green B Positive, B: Rhodamine 123 Positive C: Mito-tracker Red Positive; and D: no staining).
Figure 6:
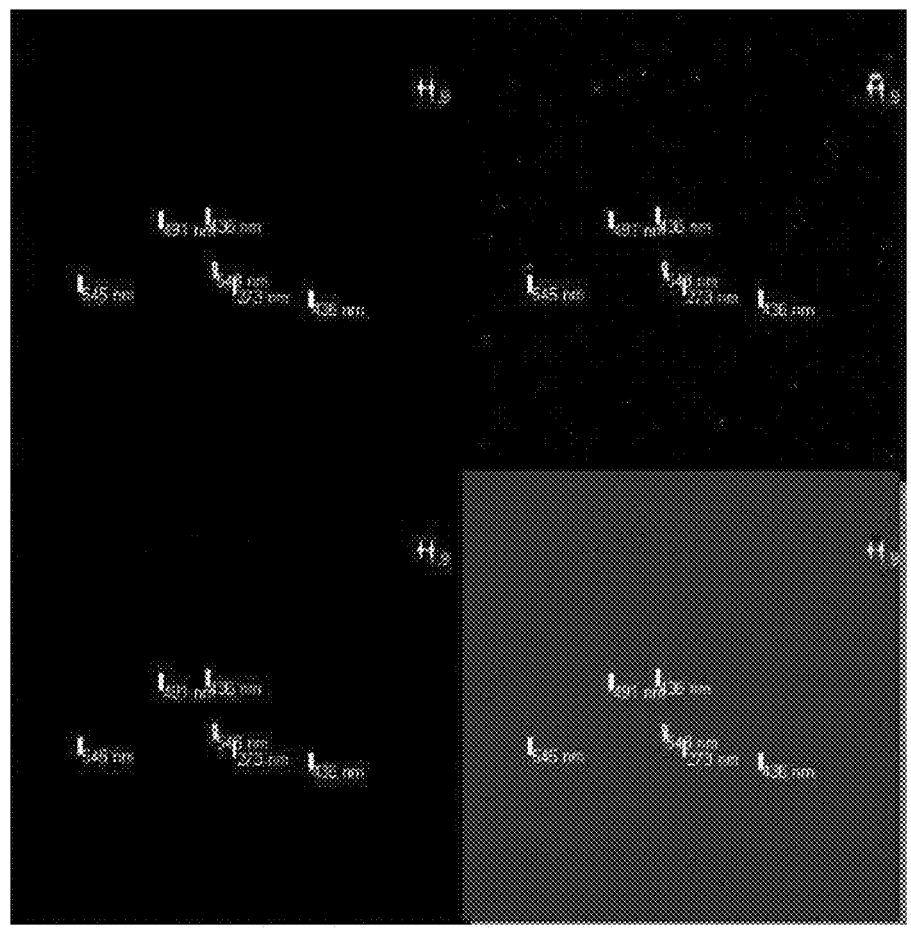
FIG. 6 shows the size (50 nm to 800 nm) of luterion by measuring the fluorescence staining region size of the luterion (A: Janus Green B reaction size measurement; B: Rhodamine 123 reaction size measurement; C: Mito-tracker red reaction size measurement: D: no staining reaction size measurement).
Figure 7:
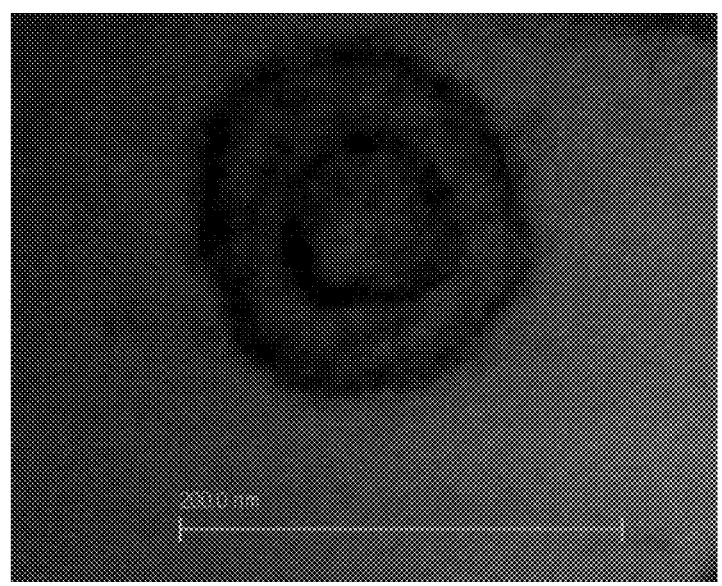
FIG. 7 is an image obtained by TEM electron microscope, showing that the luterion has a double membrane structure.

It is confirmed that mitochondria are colored by Janus green B and fluorescent dye Rhodamine 123, Mitotracker, Acridine orange, and DAPI, and the luterion and luterial also are colored by the same coloring agent as those of mitochondria (See FIGS. 1 through 6). They have a membrane structure with a double membrane similar to that of mitochondria and has a structure in which the internal cristae structure is not completed (See FIG. 7). It is observed in the same laser wavelength range as the mitochondria. Thus, they may also be referred to as pseudo-mitochondria, mitochondrial analog, or proto-mitochondria.

The luterion is abundant in trunk portions of plants, and the present inventors have separated the plant-derived luterion and examined the characteristics thereof to file Korean patent application (Korean Patent Application No. 10-2015-0001195). The separated luterion has the characteristics of:

(a) including a circular or oval shape in size (50 nm to 200 nm) smaller than red blood cells, and having motility in the normal;

(b) having a nucleic acid;

(c) showing a similar reaction to mitochondria upon immunochemical fluorescence staining;

(d) indicating fusion and/or fission ecological form;

(e) maturing to a size of up to 300 nm in the absence of fusion, maturing into pseudo-mitochondria containing DNA, and showing a mitochondria-like structure on an image obtained by a scanning electron microscope (SEM) or transmission electron microscope (TEM);

(f) increasing a size thereof in several thousand nm when fusion occurs;

(g) producing mutant luterial whose size is larger than that of the normal origin (longer diameter is 500 nm or more) and whose shape is uneven in the case of a derivate from a cancer patient; and (h) showing a light reaction different from exosomes.

Further, it may have one or more of the following characteristics of:

(i) showing autofluorescence;

(j) producing ATP at a size of 200 nm to 400 nm;

(k) adherence;

(l) a double membrane structure;

(m) bursting the mutated luterial under certain conditions, and having a stemness after the mutated luterial bursts;

(n) having a function of adjusting p53 gene and telomere; and (o) containing a surface antigen of CD39 or CD73.

Further, the luterion does not dissolve or disappear in a short time at room temperature, and it is not mutated by fusion even when stored for a long time.

It is anticipated that the luterion and luterial are involved in not only signaling, cell differentiation, cell death, but also regulation of cell cycle and cell growth. The present inventors have found that the luterial is closely related to the diagnosis of cancer (Korean patent application No. 10-2013-0082060, International patent application No. WO2015/005553).

Further, it was confirmed that the expression of telomerase increases and the length of telomere increases by the luterion treatment in normal cells (Korean patent application No. 10-2015-00007522), and the luterion showed anti-aging activity increasing telomerase activity in normal cells.

According to the present disclosure, "normal cell" means a cell having a normal aging process, which is not a cell having a phenotype undergoing infinite proliferation due to the increased telomerase activity such as cancer cells.

The term "telomerase" of the present disclosure means a ribonucleic acid protein that catalyzes the addition of telomeric repeats to the terminals of the telomeres. Telomere is a long stretch of repeating sequence covering the terminal of a chromosome and is believed to stabilize the chromosome. In humans, telomere is typically 7 kb to 10 kb in length and contains multiple repeats of the sequence -TTAGGG-. Telomerase is not expressed in most adult cells, and telomere length reduces the continuous replication of the original. When cell replication reaches a certain number of times or more, telomere gradually shrinks, causing the cells to enter the terminal collapse stage, which causes the cells to age. Telomerase is inactive in somatic cells, but is active in 90% of cancer cells, and telomerase inhibitors can be useful in inhibiting cancers.

In one exemplary embodiment of the present disclosure, telomerase expression and activity are increased by the luterion treatment in normal cells, whereas the luterion treatment of cancer cell lines reveals that telomerase expression and activity are decreased. In other words, it can be confirmed that the luterion suppresses only the telomerase activity of cancer cells.

According the first aspect of the present disclosure, the present disclosure relates to a composition for inhibiting telomerase activity of cancer cells, comprising luterion as an active ingredient.

According to the present disclosure, it is confirmed that there is no effect on the cell viability when normal cells are treated with the luterion, while there is a strong inhibitory effect on proliferation of the cancer cell lines when treated with variously derived luterions. In other words, it is confirmed that the luterion inhibits the proliferation of cancer cells without affecting normal cells.

Further, in one exemplary embodiment of the present disclosure, it is confirmed that the extract of *Rhus verniciflua* stokes containing the luterions induces dose-dependent inhibition of the telomerase activity in various cancer cell lines including the lung cancer cell line A549, pancreatic cancer cell line AsPc-1, breast cancer cell line BT-20 and colon cancer cell line HT-29. The same extract yet without the luterions is ineffective for inhibiting the telomerase activity. The purified luterions isolated from the extract is comparably effective in inhibiting the telomerase activity.

In addition, it is confirmed that there are changes in expression of genes implicated in the modulation of cancer such as Sirt1, p53 or mTOR. When referring to FIGS. 22 through 26, it is confirmed that the luterion up-regulates or restores the expression of genes such as Sirt1, or p53, or down-regulates or inhibits the expression of mTOR, after oral intake of the luterion to mice.

It has been documented in multiple studies that Sirt11 works as a tumor suppressor through its anti-proliferative activities. Sirt1, a NAD+-dependent protein deacetylases, is known to block nuclear translocation of p53 via its deacetlation and increases the passage of the accumulated cytosolic p53 to mitochondria, thus, increasing p53-mediated transcription independent apoptosis (Jingjie Yi, et al. Biochim Biophys Acta. 2010 August; 1804(8): 1684-1689). In one exemplary embodiment of the present disclosure, the luterion was shown to consistently upregulate the exression of Sirt1 in spleen, lung and liver in mice (FIGS. 22 through 24), implicating the anti-proliferative role of luterion via promoting of apoptosis. Furthermore, the luterion was shown to upregulate a well-known tumor suppressor p53 in spleen, liver and lung, further implicating the role of the luterion in tumor suppresion.

The luterion also downregulated the mammalian target of rapamycin (mTOR). Studies have demonstrated that proteins regulating mTOR as well as some of the targets of the mTOR kinase, are overexpressed or mutated in cancer. Rapamycin, the naturally occurring inhibitor of mTOR, along with a number of other rapamycin analogs (rapalogs) was shown inhibit the cell proliferation in multiple tumor models, both in vitro and in vivo, via downregulation of mTOR. As shown in FIGS. 22 through 26, the luterions consistently downregulatd mTOR expression in spleen, mung, liver, muscle and testis in mice, to the level comparable to rapamycin. Taken together, the regulation of Sirt1, p53 and mTOR expressions by the luterion strongly implicates the role of luterion as an anti-tumor agent.

In an another exemplary embodiment of the present disclosure, the prevention or treatment of cancer could be achieved by demethylation of promoters such as RAR-beta-2, APC, DAP-K, MGMT, GST-P1 or ppENK.

Further, the prevention or treatment of cancer could be achieved by repair of point mutation in genes of which expression causes a cancer by the luterion treatment. For example, by the treatment of the luterion, V599E of BRAF is repaired to V599V.

In addition, the prevention or treatment of cancer could be achieved by downregulation of overexpressed genes of which expression causes a cancer by the treatment of the luterion. For example, by the treatment of the luterion, overexpressed Her-2/Neu gene is downregulated.

According the second aspect of the present disclosure, the present disclosure relates to a pharmaceutical composition for preventing or treating a cancer, comprising the luterion as an active ingredient.

The luterion of the present disclosure may be derived from *Rhus verniciflua*, but is not limited thereto. For example, the luterion can be used as one derived from medicinal plants described in Tables 1 to 4. The luterion is present in all plants and animals and thus is not limited to the medicinal plants described in Tables 1 to 4.

TABLE 1

| Group | Name of Herb | Scientific Name |
|---|---|---|
| A | Ganghwal | *Ostericum koreanum* Maximowicz |
|  | Dokhwal | *Aralia continentalis* Kitagawa |
|  | Hyeonggae | *Schizonepeta tenuifolia* Briquet |
|  | Bangpung | *Saposhnikovia divaricata* Schischkin |
|  | Saengjihwang | *Rehmannia glutinosa* Liboschitz ex Steudel |
|  | Bongnyeong | *Poria cocos* Wolf |
|  | Jeonho | *Angelica decursiva* Franchet et Savatier |
|  | Chajeonja (jilkyungee) | *Plantago asiatica* Linne |
|  | Jigolpi (gugija) | *Lycium chinense* Miller |
|  | Siho | *Bupleurum falcatum* Linne |
|  | Taeksa | *Alisma orientale* Juzepzuk |
|  | Moktong | *Akebia quinata* Decaisne |
|  | Hyeonsam | *Scrophularia ningpoensis* Hemsley |
|  | Gwalluin | *Trichosanthes kirilowii* Maximowicz |
|  | Jeoryeong | *Polyporus umbellatus* Fries |
|  | Hwangnyeon | *Coptis japonica* Makino |
|  | Gosam | *Sophora flavescens* Solander ex Aiton |
|  | Hwangbaek | *Phellodendron amurense* Ruprecht |
|  | Jimo | *Anemarrhena asphodeloides* Bunge |
|  | Sukjihwang | *Rehmannia glutinosa* Liboschitz ex Steudel |
|  | Sansuyu | *Cornus officinalis* Siebold et Zuccarini |
|  | Mokdanpi | *Paeonia suffruticosa* Andrews |
|  | Bokbunja | *Rubus coreanus* Miguel |
|  | Indongdeung | *Lonicera japonica* Thunberg |

TABLE 1-continued

| Group | Name of Herb | Scientific Name |
|---|---|---|
|  | Bakha | *Mentha arvensis* Linne var. *piperascens* Malinvaud ex Holmes |
|  | Chija | *Gardenia jasminoides* Ellis |
|  | Yeongyo | *Forsythia viridissima* Lindley |
|  | Ubangja | *Arctium lappa* Linne |

TABLE 2

| Group | Name of Herb | Scientific Name |
|---|---|---|
| C | MihuDeung (Darae) | *Actinidia arguta* PLANCH |
|  | Mihudo | *Actinidia arguta* Fructus |
|  | mokgwa | *Chaenomelis* Fructus |
|  | Podogeun | *Vitis vinifera* Radix |
|  | Nogeun | *Phragmitis* Rhizoma |
|  | Aengdo | *Prunus tomentosa* Thunb |
|  | Ogapi | *Acanthopanax sessiliflorum* SEEM |
|  | Songhwabun | *Pinus densiflora* S. et Z |
|  | Jeodugangbansi | rice bran on a mallet head |
|  | Cheongsongjeol | *Pinus tabulaeformis* |
|  | Gyomaekmi | *Semen Fagopyri* |

TABLE 3

| Group | Name of Herb | Scientific Name |
|---|---|---|
| U | Sumac | *Rhus verniciflua* |
|  | Cheongung | *Cnidium officinale* Makino |
|  | Danggwi | *Angelica Gigas* Nakai |
|  | Jinpi | *Citri Unshius* Pericarpium |
|  | Jeokhasuo | *Polygonum multiflorum* Thunberg |
|  | Baeksuo | *Cynanchum wilfordii* Hemsley |
|  | Ginseng | *Panax ginseng* C. A. Meyer |
|  | Baekchul | *Atractylodes japonica* Koidzumi |
|  | Changchul | *Atractylodes lancea* De Candlle |
|  | Geongang (ginger) | *Zingiber officinale* Roscoe |
|  | Yukgye (cinnamon) | *Cinnamomum cassia* Presl |
|  | Cheongpi (mandarin tree) | *Citrus unshiu* Markovich |
|  | Gwakhyang | *Agastache rugosa* O. Kuntze |
|  | Jasoyeop | *Perilla frutescens* Britton var. *acuta* Kudo |
|  | jujube | *Zizyphus jujuba* Miller var. *inermis* Rehder |
|  | Gamcho | *Glycyrrhiza uralensis* Fischer |
|  | Buja | *Aconitum carmichaeli* Debeaux |
|  | Hyangbuja | *Cyperus rotundus* Linne |
|  | Hwanggi | *Astragalus membranaceus* Bunge |
|  | Baekjagyak | *Paeonia lactiflora* Pallas |
|  | Sohoehyang | *Foeniculum vulgare* Miller |
|  | Goryanggang | *Alpinia officinarum* Hance |
|  | Daebokpi | *Areca catechu* Linne |
|  | Banha | *Pinellia ternata* Breitenbach |
|  | Namseong | *Arisaema amurense* Maximowicz var. *serratum* Nakai |
|  | Ikji | *Alpinia oxyphylla* Miguel |
|  | Jisil (trifoliate orange) | *Poncirus trifoliata* Rafinesque |
|  | Hubak | *Magnolia ovobata* Thunberg |
|  | Mokhyang | *Aucklandia lappa* Decne |
|  | Osuyu | *Evodiae rutaecarpa* Bentham |
|  | Pagoji | *Psoralea corylifolia* Linn |
|  | Chongbaek(Root of green onion) | *Allium fistulosum* Linn |
|  | Sain | *Amomum villosum* Loureiro |
|  | Sansa | *Crataegus pinnatifida* Bunge |

TABLE 4

| Group | Name of Herb | Scientific Name |
|---|---|---|
| G | Mahwang | *Ephedra sinica* Staph |
| | Gamguk | *chrysanthemum indicum* Linne |
| | Gilgyeong (balloon flower) | *Platycodon* grandiflorum |
| | Haengin (apricot tree) | *Prunus armeniaca* var. *ansu* Max. |
| | Baekji | *Angelica dahurica* BENTH. et HOOK |
| | Maengmundong | *Liriope muscari* BALL |
| | Cheonmundong | *Asparagus cochinchinensis* Men |
| | Sanyak (Chinese Yam) | *Dioscorea japonica* THUNB |
| | Sanjoin | *Zizyphus* jujube |
| | Yongannyuk | *Dimocarpus longan* Lour |
| | Wonji | *Polygala* tenuifolia |
| | Seokchangpo | *Acorus graminens* SOLAND |
| | Omija | *Schizandra chinensis* BAALL |
| | Geonyul | *Castanea crenata* S.et Z. |
| | Uiiin | *Coix lachryma-jobi* var. *ma-yuen* |
| | Nabokja (daikon) | *Raphanus sativus* L |
| | Galgeun (kudzu) | *Pueraria* thunbergiana |
| | Hwanggeum | *Scutellaria baicalensis* GEORG |
| | Gobon | *Angelica tenuissima* NAKAI |
| | Nogyong | *Cervi Parvum* Cornu |
| | Daehwang | *Rheum palmatum* |
| | Seungma | *Cimicifuga heracleifolia* KOM |
| | Baekjain | *Biota orientalis* ENDL |
| | Sangbaekpi (mulberry) | *Morus alba* L |
| | Gwandonghwa | *Tussilago* farfara |
| | Baekgwa | *Gingko biloba* L |
| | Sahyangpul | *Thymus* vulgaris |
| | Jogak | *Gleditsia japonica* Miguel var. *koraiensis* Nakai |

Further, the luterion used in the present disclosure has, but is not limited to, a density of 1 or less, a density higher than those of fat and lipid, a density lower than that of protein, and thus can be separated from plants by steam distillation.

The luterion used in the present disclosure can be isolated from plants by the steam distillation method as below:

(a) adding a solvent to a plant and shaking it while bubbling intermittently with air or oxygen at 50° C. to 90° C.;

(b) collecting vapor or gas vaporized by the shaking and then cooling to obtain a condensate;

(c) filtering the obtained condensate using a filter having pores of from 0.8 μm to 1.2 μm;

(d) centrifuging the filtered condensate; and (e) separating the plant-derived luterion from the centrifuged supernatant.

The luterion used in the present disclosure can be used by adding water to the luterion and culturing the same at 18° C. to 30° C. under IR light irradiation.

In one embodiment of the present disclosure, there is provided a method and composition for treating cancer by inhibiting telomerase of mammalian cancer cells and inhibiting telomerase-positive cells. The composition of the present disclosure includes a therapeutically effective amount of the luterion in a pharmaceutically acceptable carrier or salt.

The composition of the present disclosure may also be used for treatment of other telomerase related conditions or diseases, such as other hyperproliferative such as psoriasis or autoimmune disorders, rheumatoid arthritis, immune system disorders requiring immune system suppression, immune system response to poison ivy or poison oak.

Further, it will be appreciated that therapeutic benefits for cancer treatment is carried out by combining telomerase inhibitors of the present disclosure as well as other telomerase inhibitors as described in U.S. Pat. Nos. 5,656,638; 5,760,062; 5,767,278; 5,770,613 and 5,863,936 with other anti-cancer agents. The selection of such combinations vary, but is not limited to, depending on a type of a disease, an age and general health state of a patient, aggressiveness of disease progression, TRF length and telomerase activity of the diseased cells to be treated, and a patient's tolerance to an agent comprising the combination. For example, when the cancer progression has reached an advanced state, the telomerase inhibitory compound of the present disclosure may be used in conjunction with other agents effective to reduce cancer size and therapeutic regimens (e.g., radiation therapy, surgery, chemotherapy and/or hormone therapy). Further, in some cases, it may be recommended that the telomerase inhibitor of the present disclosure is used in combination with one or more agents that treat side effects of the disease, such as analgesics, or agents that are effective in stimulating the immune response of the patient (e.g., a colony stimulating factor).

The luterion composition of the present disclosure may be administered to a human or animal subject by any suitable means.

The composition may be orally or parenterally, intramuscularly, intracerebrally, vascularly (including intravenously), subcutaneously, intranasally, intracardiacly, intracerebrally, intraperitoneally, or transdermally administered to a human or animal subject.

Generally, the composition may be administered by injection, and may preferably be administered in the form of vascular injection (e.g., intravenous) or intramuscular injection, and the route necessary for administration may be adjusted depending on the characteristics of the patient.

The composition of the present disclosure may be formulated for any suitable means including parenteral, intramuscular, intracerebral, vascularly (including intravenously), intracardiac, intracerebral, intraperitoneal, subcutaneous, intranasal, or transdermal administration. The composition for parenteral administration may also include a buffer, a diluent, and other suitable additive, and may include a sterile aqueous solution.

The composition of the present disclosure may contain a pharmaceutically acceptable carrier, a thickener, a diluent, a buffer, a preservative, and other pharmaceutically acceptable carrier, or an excipient in addition to the luterion, and may be formulated into a pharmaceutical composition.

"Pharmaceutically acceptable carrier (excipient)" is an agent for delivering one or more nucleic acids to a patient or a pharmacologically acceptable carrier that can be used in the pharmaceutical composition of the present disclosure and is other pharmacologically inactive, and includes, but is not limited to, ion exchange, alumina, aluminum stearate, lecithin, serum proteins (such as human serum albumin), buffer substances (such as various phosphates, glycine, sorbic acid, potassium sorbate, partial glyceride mixtures of saturated vegetable fatty acids), water, salts, or electrolytes (such as protamine sulfate, disodium hydrogen phosphate, potassium hydrogen phosphate, sodium chloride, and zinc salts), colloidal silica, magnesium trisilicate, polyvinylpyrrolidone, cellulose-based substrate, polyethylene glycol, sodium carboxymethylcellulose, polyarylate, wax, polyethylene-polyoxypropylene-barrier polymer, polyethylene glycol, wool fat, and the like.

The pharmaceutical composition may be in the form of a sterile injectable preparation as a sterile injectable aqueous or oleaginous suspension. The suspension may be formulated according to techniques known in the art using suitable dispersing or wetting agents (e.g., Tween 80) and suspending agents. The sterile injectable preparation may also be a sterile injectable solution or suspension (e.g., a solution in 1,3-butanediol) in a non-toxic parenterally acceptable diluent or solvent. Vehicles and solvents that may be acceptably used include mannitol, water, Ringer solution, and an isotonic sodium chloride solution. In addition, sterile, non-volatile oils are conventionally employed as a solvent or suspending medium. For this purpose, any non-volatile oil with low irritation, including synthetic mono- or diglycerides, may be used. Fatty acids such as oleic acid and its glyceride derivatives are useful in injection formulations as well as pharmaceutically acceptable natural oils (e.g., olive oil or castor oil), especially those polyoxyethylated.

The composition of the present disclosure is administered in a therapeutically effective amount. The route of administration and the required regimen dosage may be determined according to various parameters, in particular according to the severity of the condition, age, and weight of a patent to be treated. Optimal dosages may vary depending on the relative potency of the individual constructs and may be based on EC50s found to be generally, presumably effective in in vitro and in vivo animal models. Generally, the dosage is from 0.01 mg/kg to 100 mg/kg. The age, weight, and condition's severity and frequency of the disease of a patient to be treated and routes of administration, structure's other dosage can be adjusted by administration, intramuscular injection or tissue (intravenous or subcutaneous) injection to be administrated.

The composition of the present disclosure may also be formulated as a dietary supplement or functional food for oral administration. For functional food formulations or oral pharmaceutical compositions, suitable excipients include pharmaceutical class carriers, for example, mannitol, lactose, glucose, sucrose, starch, cellulose, gelatin, magnesium stearate, sodium saccharin, and/or magnesium carbonate. For use in oral liquid formulations, the composition may be prepared in a form of a solution, suspension, emulsion, or syrup that is produced in a solid or liquid form suitable for hydration in an aqueous carrier such as aqueous saline, aqueous dextrose, glycerol, or ethanol, preferably water or normal saline. Preferably, the composition may contain small amount of non-toxic auxiliary material such as wetting agents, emulsified agents, or buffer. The luterion of the present disclosure may be incorporated into a functional food formulation or may include a medicinal plant extract.

According the third aspect, the present disclosure relates to a food composition for preventing or ameliorating cancer comprising the luterion as an active ingredient.

According the fourth aspect, the present disclosure relates to a method of preventing or treating cancer, which includes administering a composition comprising the luterion as an active ingredient.

According the fifth aspect, the present disclosure relates to a method of inhibiting telomerase activity in a cancer tissue, cancer cell or cancer patient, which comprises administering a composition comprising the luterion as an active ingredient.

According the sixth aspect, the present disclosure relates to a method for inhibiting proliferation of cancer cells, which includes administering a composition comprising the luterion as an active ingredient.

According the seventh aspect, the present disclosure relates to a use of a composition comprising the luterion as an active ingredient in the prevention or treatment of a cancer.

According the eighth aspect, the present disclosure relates to a use of a composition comprising the luterion as an active ingredient for inhibiting telomerase activity in a cancer tissue, cancer cell or cancer patient.

According the ninth aspect, the present disclosure relates to a use for preparing an anticancer composition comprising the luterion as an active ingredient.

EXAMPLES

Hereinafter, the present disclosure will be described in more detail with reference to examples. It will be understood by those skilled in the art that these embodiments are only for describing the present disclosure in more detail and that the scope of the present disclosure is not limited to these embodiments in accordance with the concept of the present disclosure.

Example 1: Isolation of Luterion 100 g of a medicinal plant, Rhus verniciflua stokes, was cut to be corresponded in 20 times to 30 times, i.e., a size of 2 liters to 3 liters container, and placed in the container. 500 g to 800 g of distilled water (preferably 6 times of the plant, i.e., 600 g), which is 5 to 8 times the amount of the plant, was charged into the vessel, and then bathing was conducted at 80° C. or lower. Bubbling with oxygen for 20 minutes to 30 minutes was performed every about 3 hours for about 8-hour bathing, so that the luterion of the plant was not entangled. The vaporized steam that is steamed at the time of extraction after the bubbling was collected in a flask. The condensed liquid obtained by cooling and condensing the collected steam was irradiated with IR light (wavelength: about 3 μm to about 1000 μm, preferably 200 μm to 600 inn) for 1 hour to 2 hours to prevent mutation of the luterion. Thereafter, the condensate was filtered using a filter having pores with a diameter of 0.8 μm or more, and only the condensate having passed through the filter was centrifuged repeatedly at 1200 rpm to 5000 rpm for 5 minutes to 10 minutes. The supernatant obtained through the centrifugation was irradiated with IR light so that luterion particles gather with motility and were separated using a pipette. The separated luterion was passed through a filter having pores with a diameter of 50 nm, so that the unfiltered luterion was washed to obtain the luterion derived from Rhus verniciflua stokes.

By these processes, the luterion having a long diameter of 50 nm to 800 nm can be obtained, which could be observed through a dark-field microscope or a confocal microscope. The obtained luterion was classified into 50 nm to 200 nm (generating stage)/200 nm to 400 nm (mature stage)/400 nm to 600 nm (splitting stage)/600-800 nm (hyper-splitting stage) depending on the sizes thereof.

In the same manner, luterion was obtained from the medicinal plants described in Tables 1 to 4.

Example 2: Telomerase Activity of Cancer Cells by Treatment with Luterion $1 \times 10^6$ cells/ml of normal cells (Fibroblast) and cancer cells (NCl-H1975, MDA-MA-468, WiDr), respectively, were inoculated on 60 mm plates. Then, after about 12 hours, the luterion isolated in Example 1 was treated at 50 μg/ml to be cultured. Cell culture was performed in a 5% $CO_2$ incubator at 37° C. using 1% FBS DMEM medium without antibiotic-antimycotic (PSF) antibiotic. Cells were harvested 48 hours after inoculation, and telomerase activity was measured.

Telomerase activity was analyzed by TRAP analysis using TRAPeze® Telomerase Detection Kit (Millipore). As a result, it was confirmed that telomerase expression and activity of cancer cells (NCl-H1975, MDA-MA-468, WiDr) was decreased by the treatment with the luterion (See part B of FIG. 11).

Figure 11:
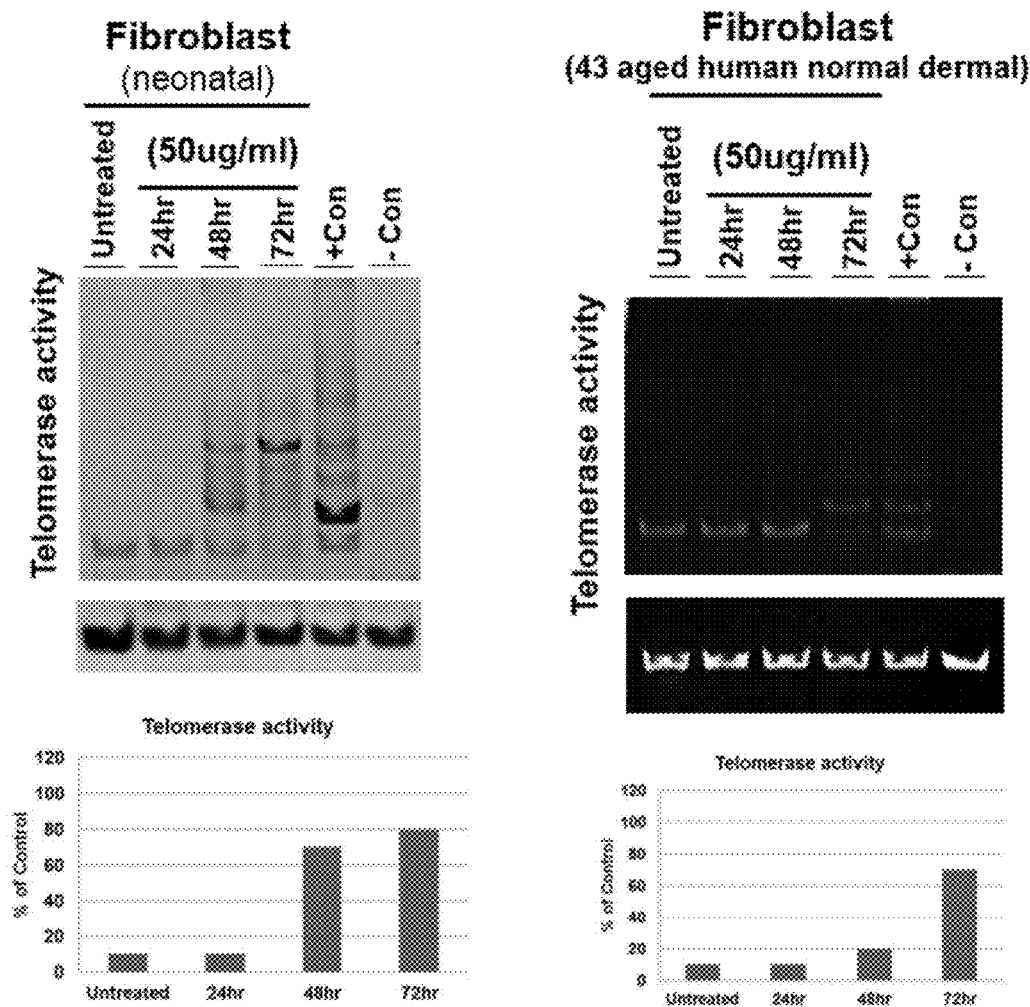
FIG. 11 shows telomerase activity in normal cells (fibroblast) and cancer cells (lung cancer, breast cancer, colon cancer) by the luterion treatment.
Figure 11:
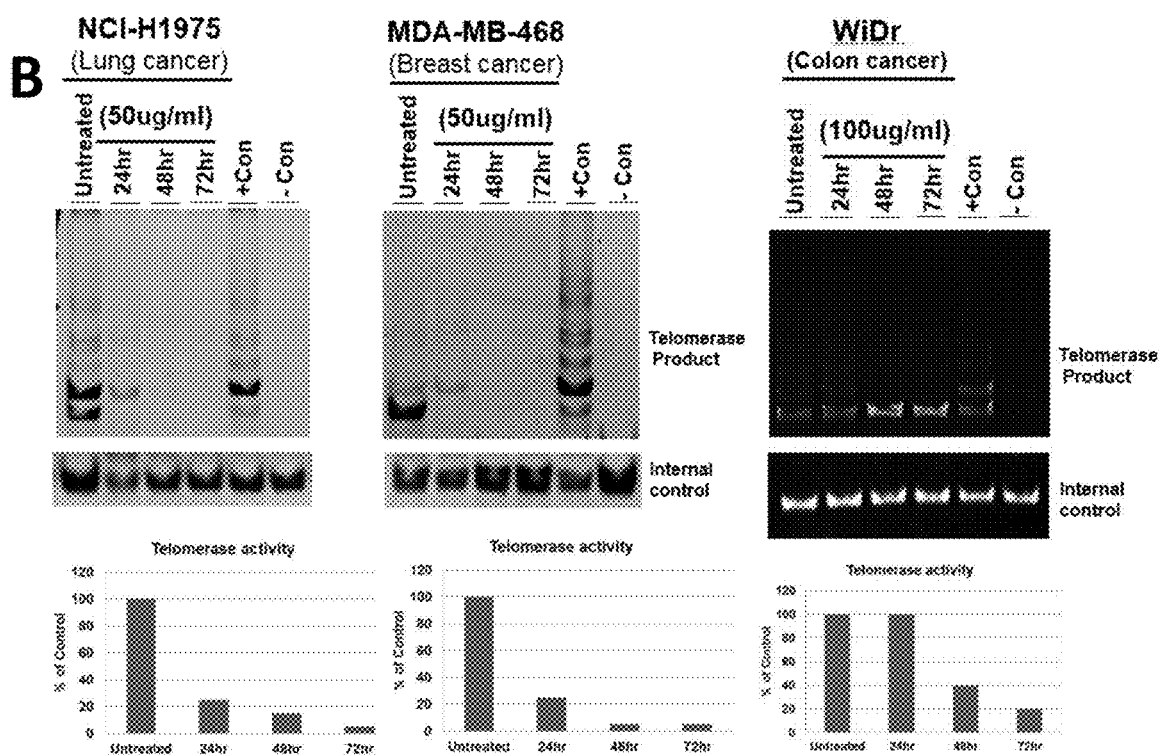

Further, as a result of performing the same experiment and analysis on a normal cell, Fibroblast, it was confirmed that telomerase expression and activity were increased in human normal cells as compared with the control group (luterion-untreated group) (See part A of FIG. 11).

Example 3: Inhibition of Cancer Cells Proliferation by Luterion Treatment

MTT analysis was performed in order to measure cytotoxicity of the luterion against cancer cells in several types of human cancer cell lines (lung cancer (NCl-H1975), colon cancer (WiDr), breast cancer (MDA-MB-486), liver cancer (HCC38), and leukemia (AGH-77)) and normal cell lines (fibroblast).

100 μl of cell suspension ($5 \times 10^4$ cells/ml) was inoculated into each of 96-well of microtiter plate having a flat bottom, and was cultured for 24 hours. Then, culture medium was changed to have the luterion having various concentrations, and again the result was cultured for 48 hours.

Then, 100 μl of a non-aqueous yellow MTT (3-(4,5-dimethylthiazole-2-yl)-2,5-diphenyltetrazolium bromide) solution diluted 10 times with the medium was added to each well. The cells were stored in an incubator at 37° C. and 5% $CO_2$ concentration to produce formazan crystals in cells. After about 4 hours, the extra medium was removed, and 200 μl of DMSO was added to each well to dissolve the water-insoluble formazan formed in the cells, and then the absorbance at 595 nm was analyzed using a microplate reader.

Figure 12:
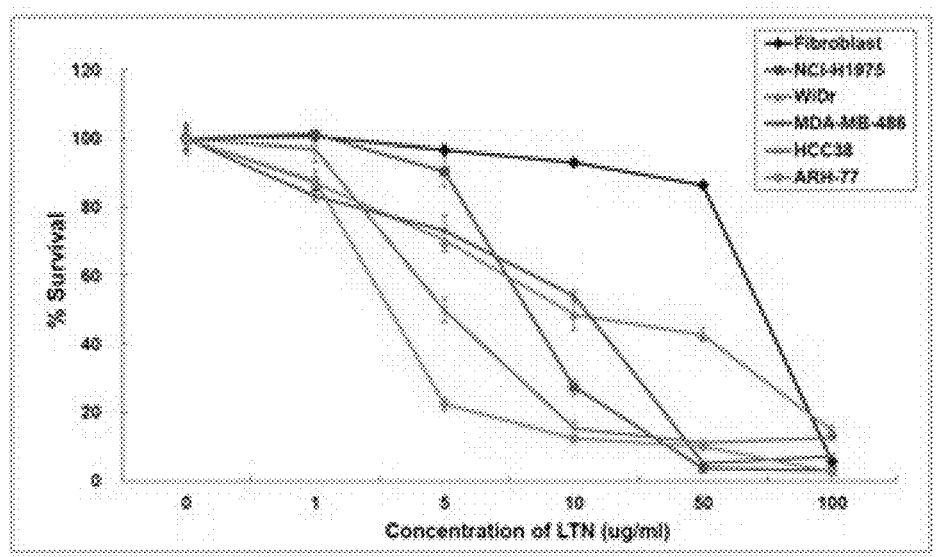
FIG. 12 shows cell viability of normal cells (fibroblast) and various cancer cells (lung cancer, breast cancer, colon cancer, liver cancer, leukemia) according to the luterion treatment concentration.

As a result of measuring the survival rate of cancer cells at the respective concentrations, which was determined as 100% of the absorbance of the control group not treated with luterion, the survival rate of cancer cells was decreased in a concentration-dependent manner, while no cytotoxicity was observed in normal cells (See FIG. 12).

Figure 13:
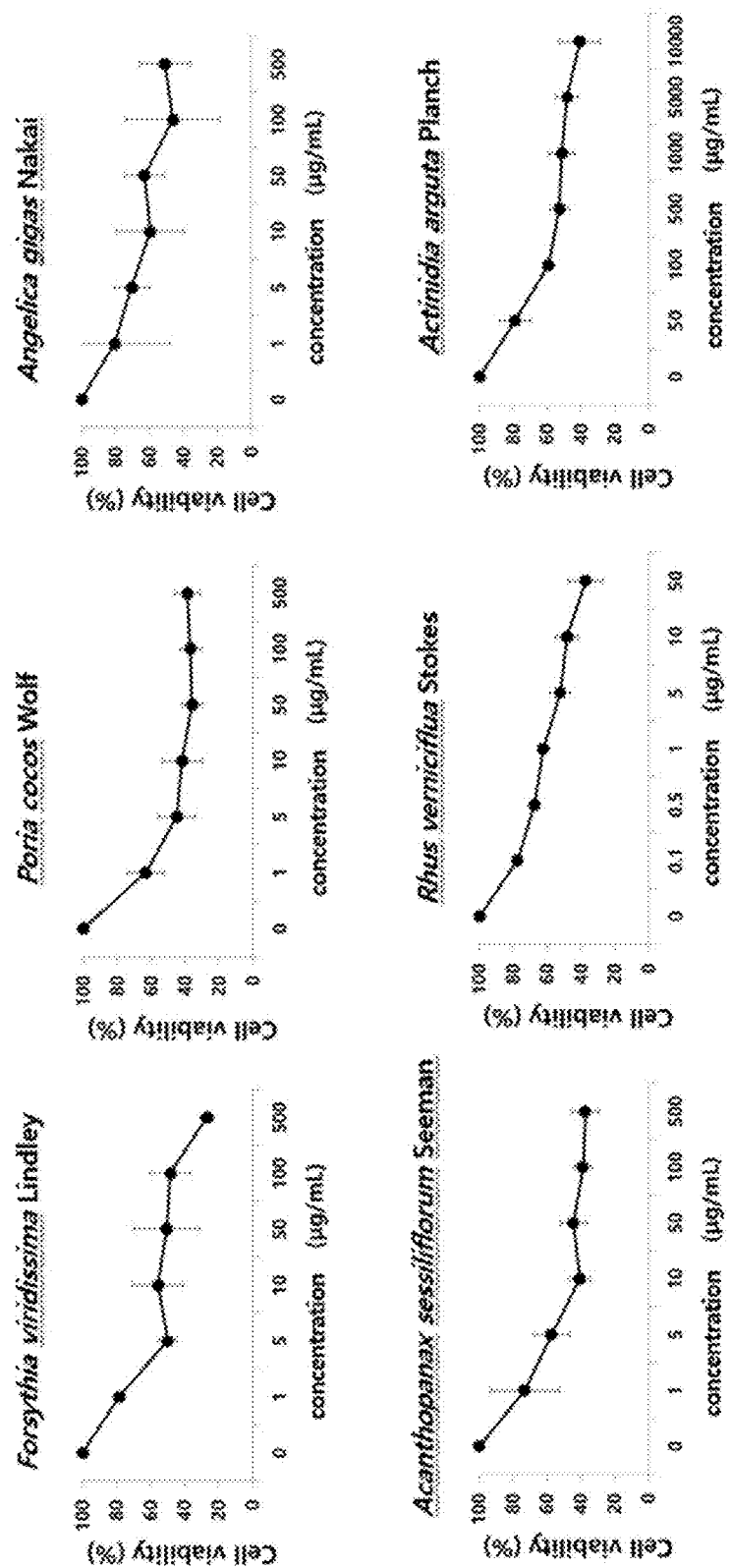
FIG. 13 shows inhibition of cell proliferation in a pancreatic cancer cell line (AsPC-1) treated with variously derived the luterion.
Figure 14:
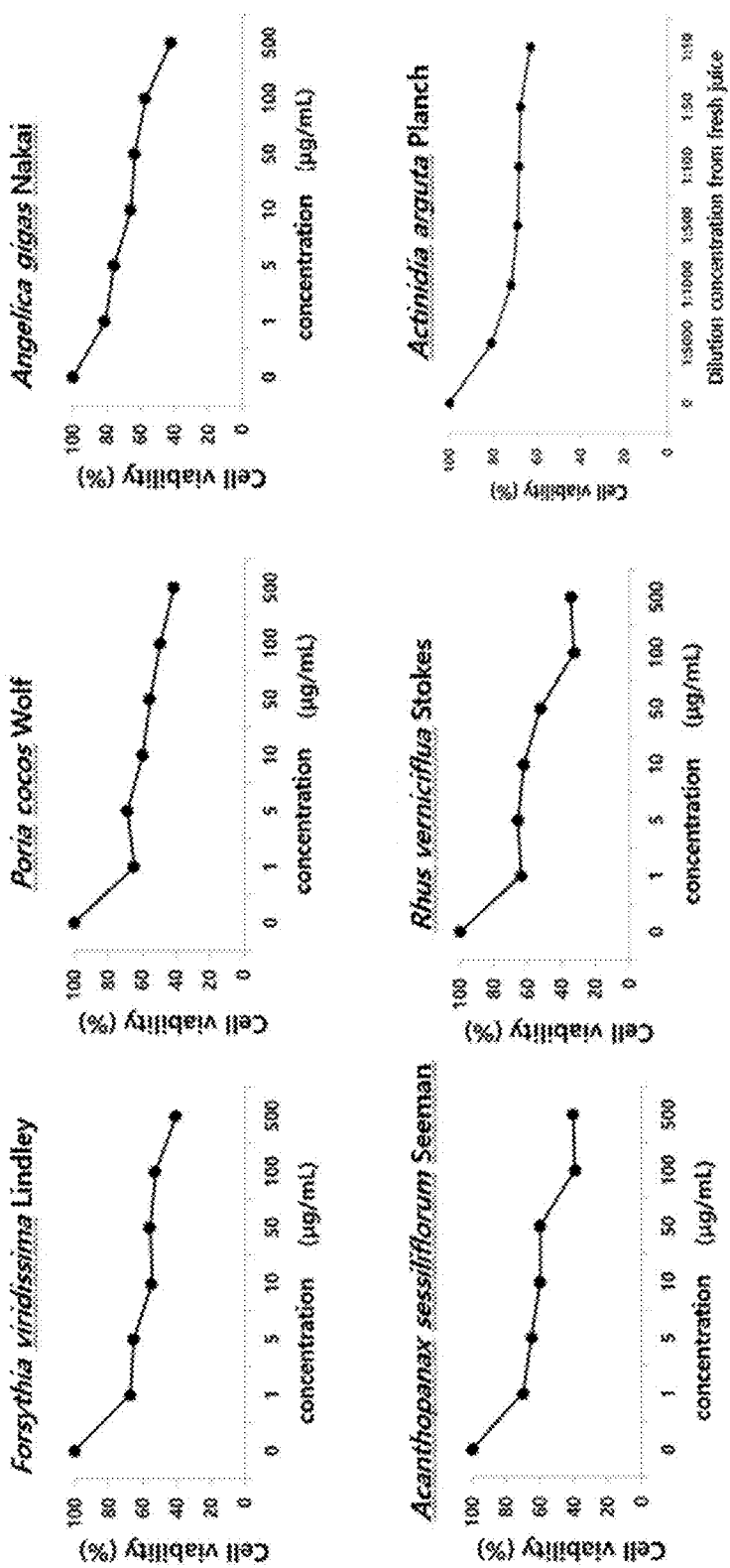
FIG. 14 shows inhibition of cell proliferation in a lung cancer cell line (A549) treated with variously derived the luterion.
Figure 15:
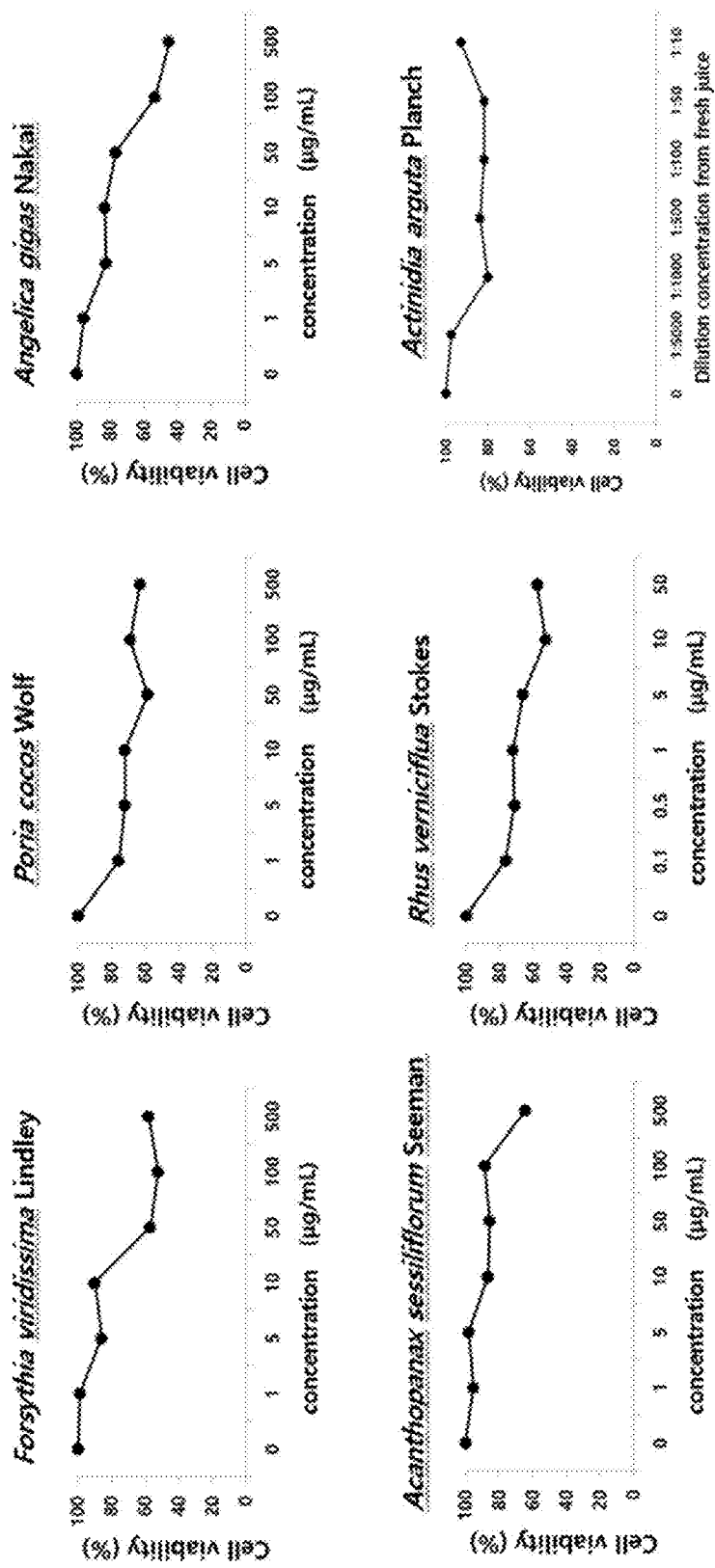
FIG. 15 shows inhibition of cell proliferation in a breast cancer cell line (BT-20) treated with variously derived luterion.
Figure 16:
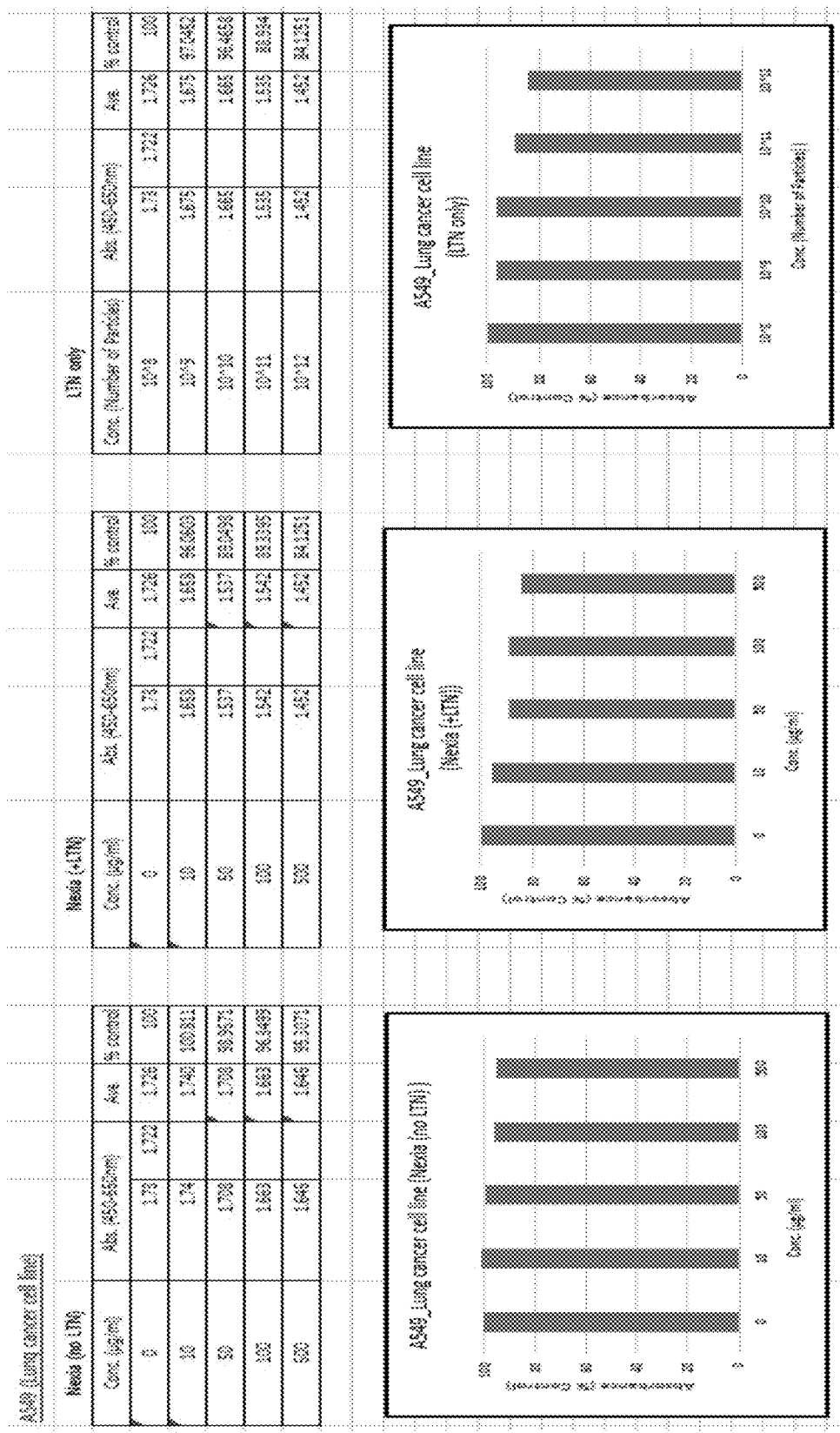
FIG. 16 shows changes in telomerase activity in lung cancer cell lines of A549 by the luterion treatment.
Figure 17:
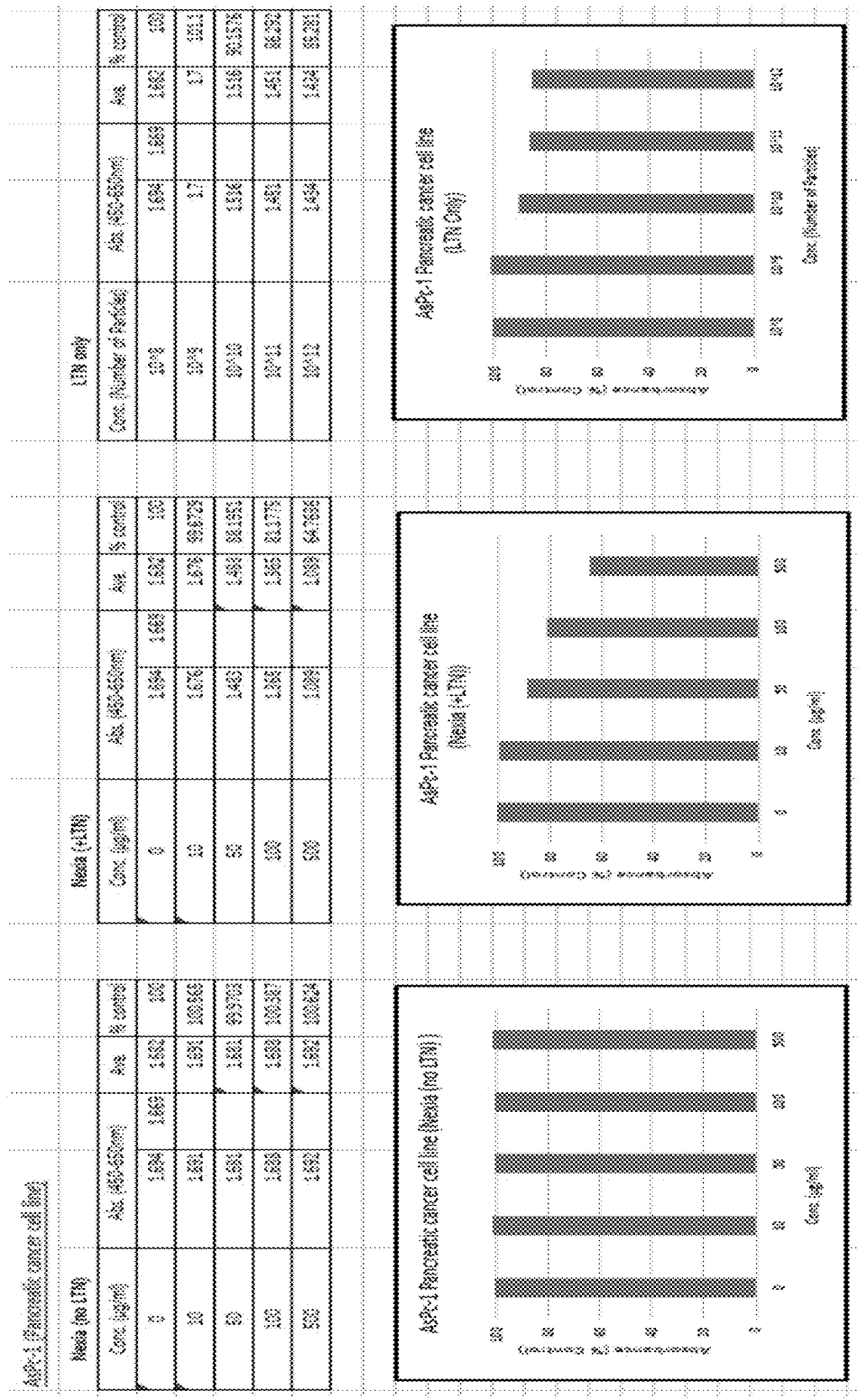
FIG. 17 shows changes in telomerase activity in pancreatic cancer cell lines of AsPc-1 by the luterion treatment.
Figure 18:
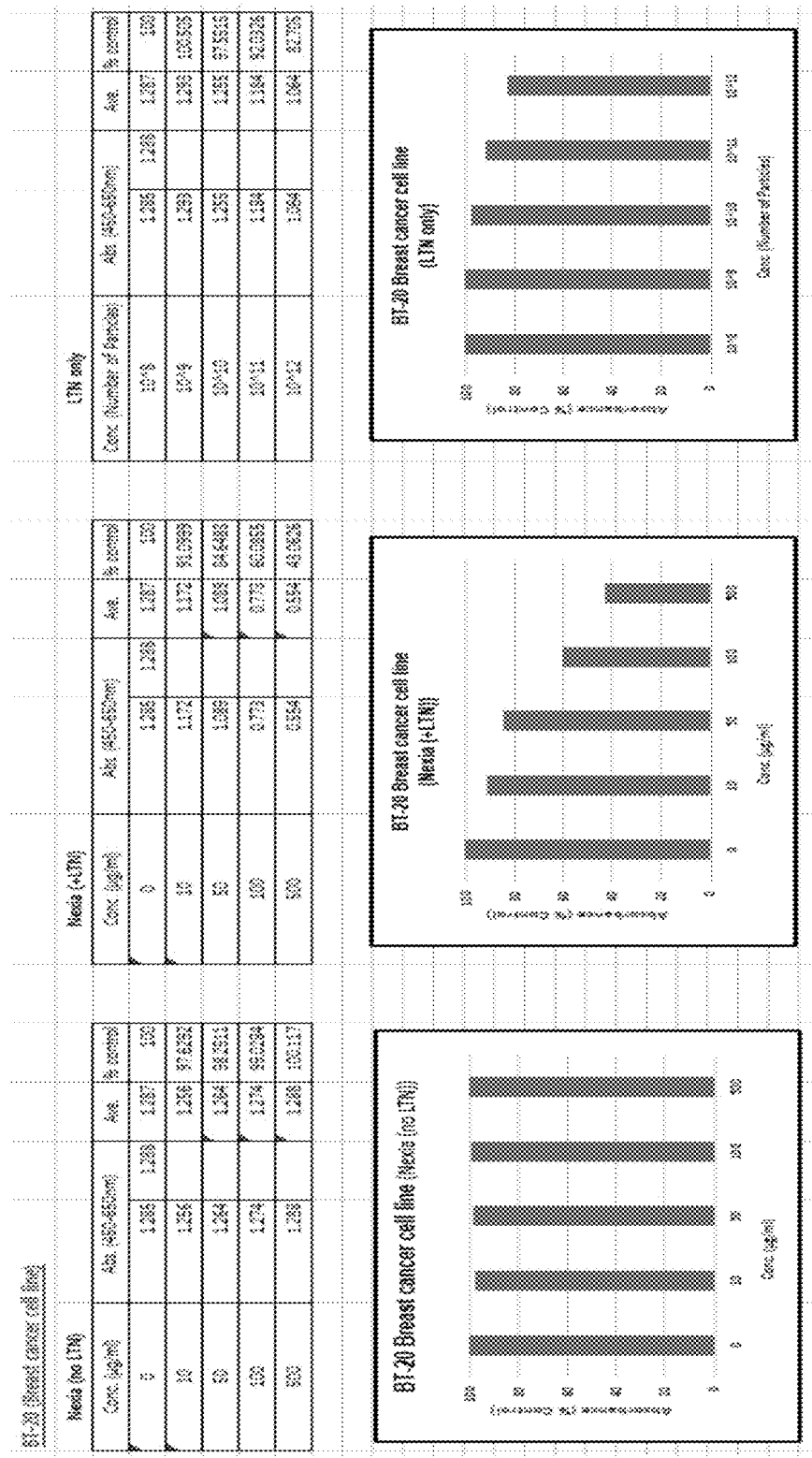
FIG. 18 shows changes in telomerase activity in breast cancer cell lines of BT-20 by the luterion treatment.
Figure 19:
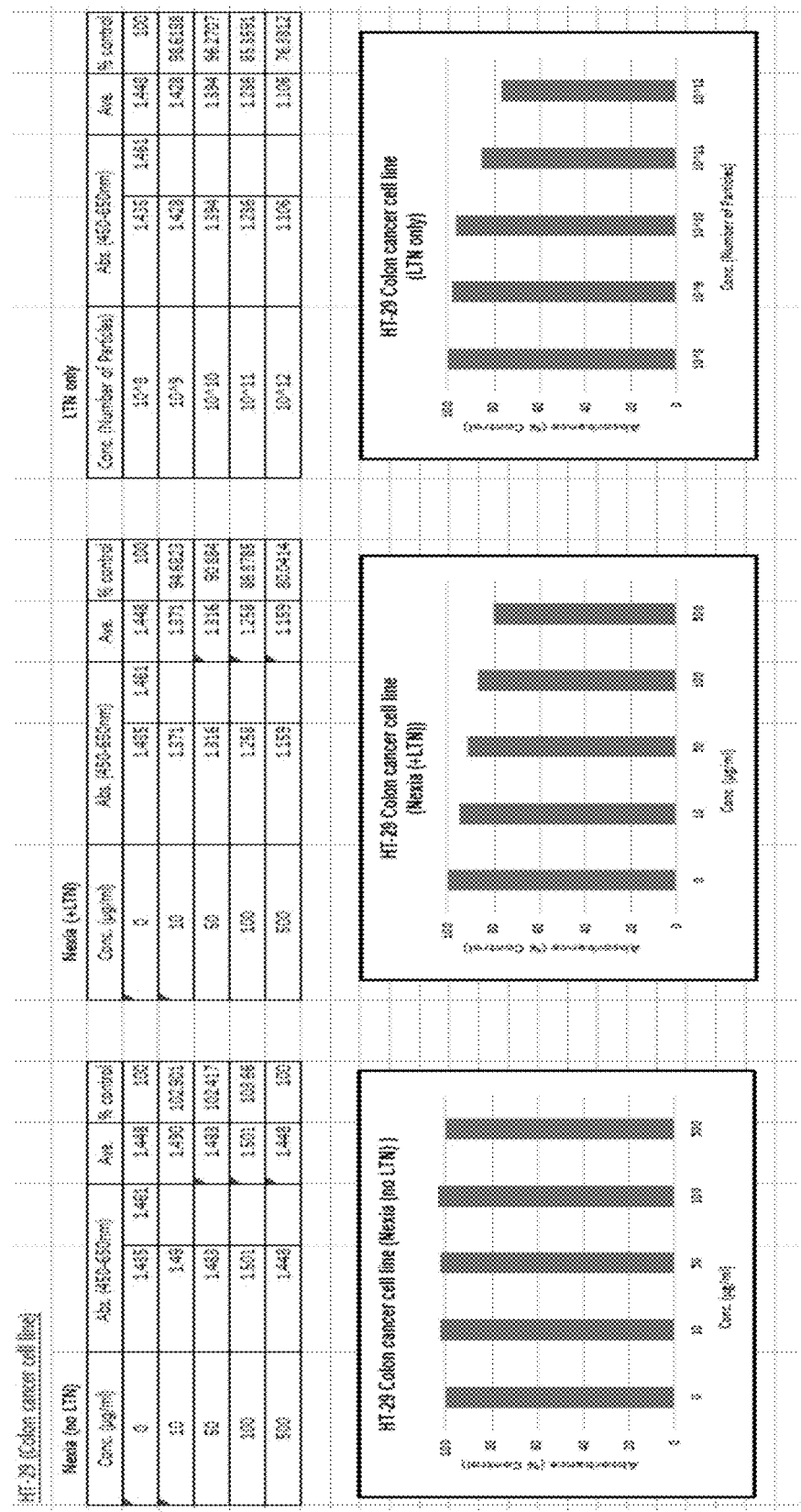
FIG. 19 shows changes in telomerase activity in colon cancer cell lines of HT-29 by the luterion treatment.
Figure 20:
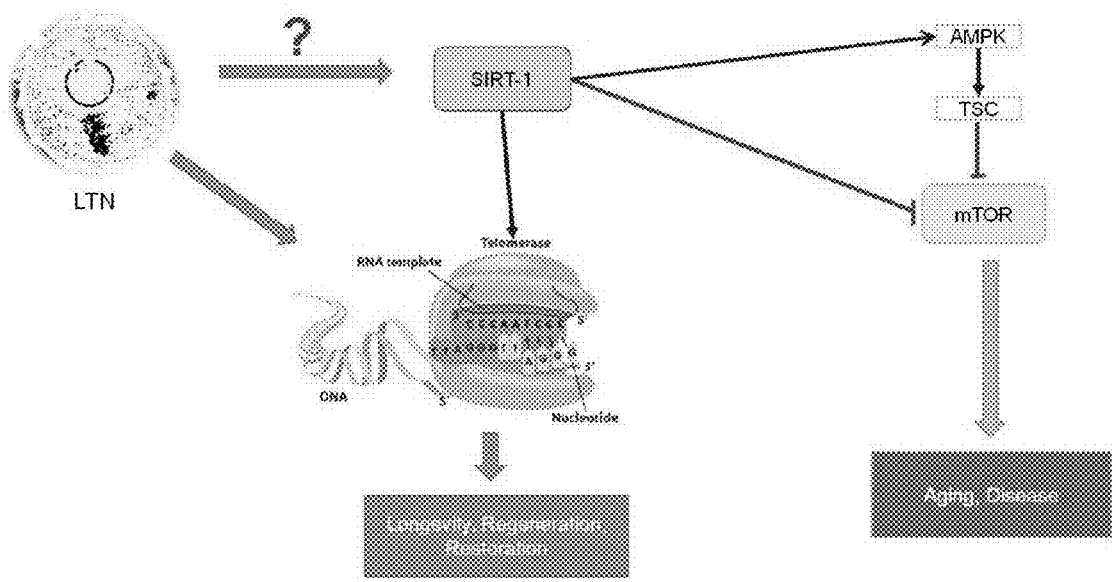
FIG. 20 shows a diagram showing the mechanism of action of the luterion in controlling telomerase activity.
Figure 21:
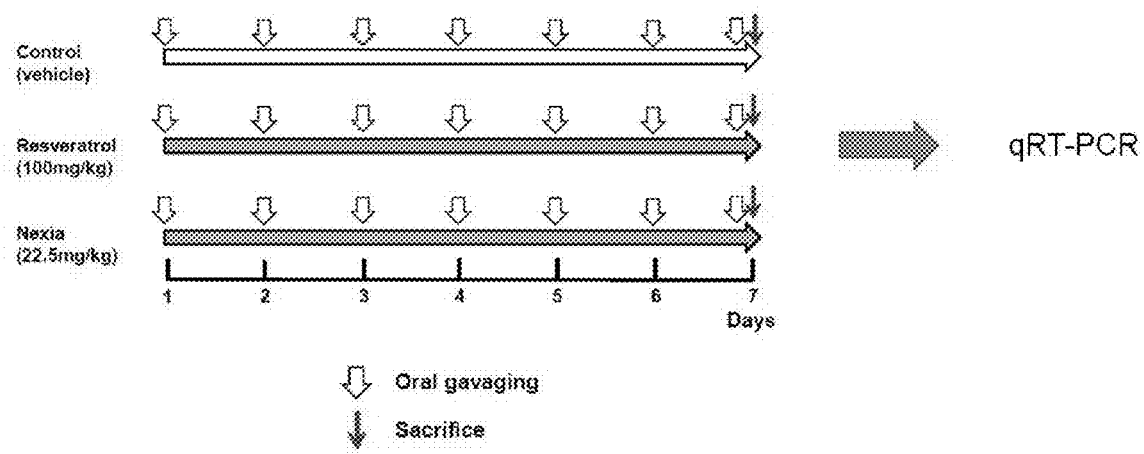
FIG. 21 shows an experimental design for measuring changes in gene expression in various organs of mice after 7-day oral gavaging of the luterion.
Figure 22:
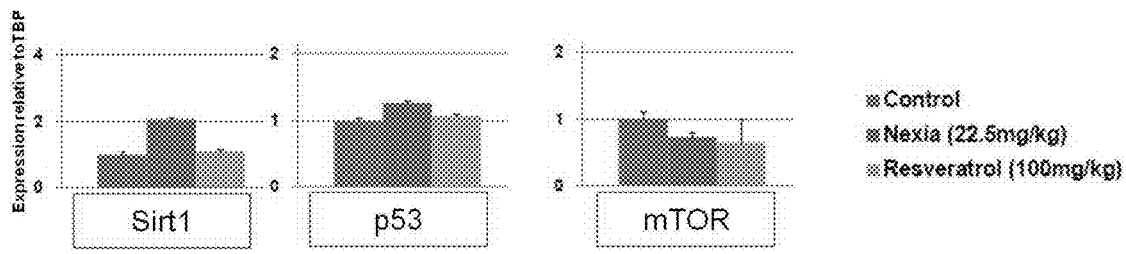
FIG. 22 shows changes in gene expression in spleen after 7-day oral intake of the luterion in comparison with resveratrol in mice.
Figure 23:
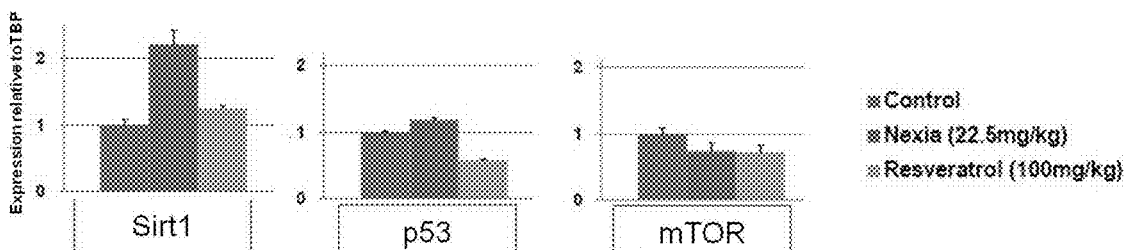
FIG. 23 shows changes in gene expression in lung after 7-day oral intake of the luterion in comparison with resveratrol in mice.
Figure 24:
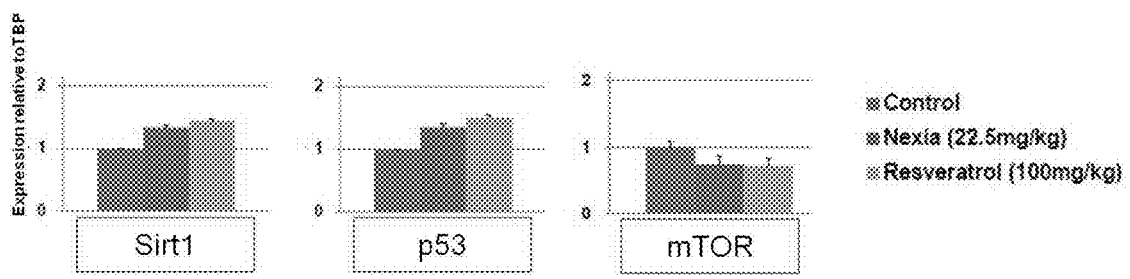
FIG. 24 shows changes in gene expression in liver after 7-day oral intake of the luterion in comparison with resveratrol in mice.
Figure 25:
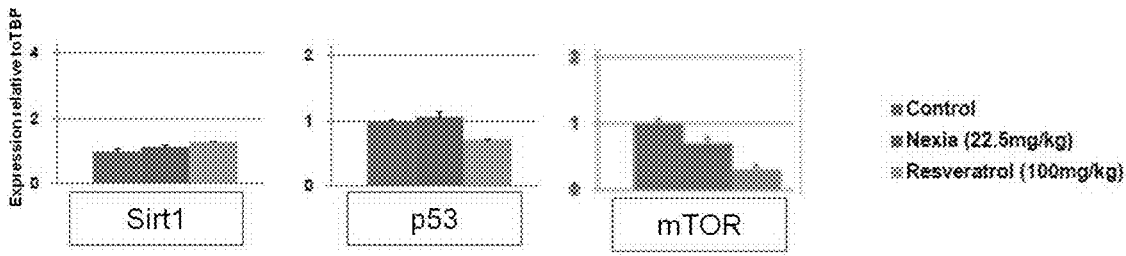
FIG. 25 shows changes in gene expression in muscle after 7-day oral intake of the luterion in comparison with resveratrol in mice.
Figure 26:
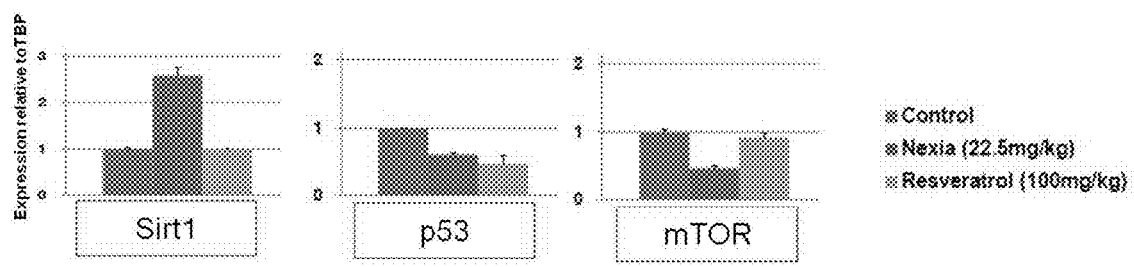
FIG. 26 shows changes in gene expression in testis after 7-day oral intake of the luterion in comparison with resveratrol in mice.

Further, it was confirmed that the cancer cell proliferation was effectively inhibited by variously derived luterion in AsPC-1 pancreatic cancer cell line, A549 lung cancer cell line, and BT-20 breast cancer cell line in addition to the cancer cell lines. The cell viability was measured in the same manner as the MTT analysis described above, and the variously derived luterion isolated by the method of Example 1 showed inhibitory effect on proliferation of cancer cells (See FIGS. 13 through 15).

Therefore, it was found that the composition comprising the luterion of the present disclosure as an active ingredient can inhibit the proliferation of cancer cells to prevent or treat a cancer.

Example 4: Control of Telomerase by Luterion (LTN): Differential Efficacy in Cancer Cell Lines Various normal and cancer cell lines grown on 96-well culture tissue plates were deprived of fetal bovine serum for 24 h prior to treatment with three types of *Rhus verniciflua* stokes extracts for 48 h and the telomerase activity of each cell lines was measured usng the Telomerase Assay Kit. It was confirmed that the telomerase activity of the cancer cell lysates of various cancer cell lines such as lung cancer cell lines A549, pancreatic cancer cell lines AsPc-1, breast cancer cell lines BT-20 and colon cancer cell lines HT-29, was dose-dependently inhibited by *Rhus verniciflua* stokes extract containing luterion but not by the same extract devoid of luterion. The pure luterion isolated from *Rhus verniciflua* extract also inhibited telomerase activity of the cancer cell lines in a dose-dependent manner, further indicating that the luterion is the key factor that suppresses telomerase activity and subsequently leads to tumor suppression.

Example 5: Measuring Changes in Gene Expression in Various Organs of Mice after 7-Day Oral Gavaging of LTN C57bL/6 mice (8 to 10 week-old male mice (20-22 g) were given *Rhus verniciflua* stoke extract containing LTN daily for 7 days via oral gavaging and sacrificed for collection of various organs including spleen, liver, lung, muscle and testis. The tissues from each organ was homogenized and lysed and isolated RNA was subjected to qRT-PCR to measure the expression level of Sirt1, p53 and mTOR transcripts. It has been documented in multiple studies that Sirt1 works as a tumor suppressor through its anti-proliferative activities. Sirt1, a NAD+-dependent protein deacetylases, is known to block nuclear translocation of p53 via its deacetlation and increases the passage of the accumulated cytosolic p53 to mitochondria, thus, increasing p53-mediated transcription independent apoptosis (Jingjie Yi, et al. Biochim Biophys Acta. 2010 August; 1804(8): 1684-1689). In one exemplary embodiment of the present disclosure, the luterion was shown to consistently upregulate the expression of Sirt1 in spleen, lung and liver in mice (FIGS. 22 through 24), implicating the anti-proliferative role of luterion via promoting of apoptosis. Furthermore, the luterion was shown to upregulate a well-known tumor suppressor p53 in spleen, liver and lung, further implicating the role of the luterion in tumor suppresion.

The luterion also downregulated the mammalian target of rapamycin (mTOR). Studies have demonstrated that proteins regulating mTOR as well as some of the targets of the mTOR kinase, are overexpressed or mutated in cancer. Rapamycin, the naturally occurring inhibitor of mTOR, along with a number of other rapamycin analogs (rapalogs) was shown inhibit the cell proliferation in multiple tumor models, both in vitro and in vivo, via downregulation of mTOR. As shown in FIGS. 22 through 26, the luterions consistently downregulated mTOR expression in spleen, mung, liver, muscle and testis in mice, to the level comparable to rapamycin. Taken together, the regulation of Sirt1, p53 and mTOR expressions by the luterion strongly implicates the role of luterion as an anti-tumor agent.

When referring to FIGS. 22 through 26, it was confirmed that the luterion up-regulates or restores the expression of genes such as Sirt1, or p53 and down-regulates or inhibits the expression of mTOR, after oral intake to mice.

Example 6: Repair of Genetic Mutations in Cancer Patients by LTN

The patient diagnosed with pancreatic cancer, yet received neither chemo- nor radio-therapy was subjected to DNA test for the known cancer markers before and after the intake of LTN.

The patient profile is as described in Table 5.

TABLE 5

| Name | Sex | Diagnosis | ChemoTx | RadioTx |
|---|---|---|---|---|
| AnOOO | M/55 | Pancreatic Cancer | none | none |

Promoters such as RAR-beta-2, APC, DAP-K, MGMT, GST-P1 or ppENK was demethylated by LTN treatment (see Table 6).

TABLE 6

| | | | Promoter Methylation | | | | | | | | |
|---|---|---|---|---|---|---|---|---|---|---|---|
| Medication | Tx period | Exam Date | p16 | RAR-beta2 | APC | DAP-K | MLH-1 | RASSF1A | MGMT | GST-P1 | ppENK | BRCA1 |
| none | | 2005 Jan. 27 | x | o | o | | | | o | x | x |
| Nexia | 7 months | 2005 Sep. 7 | x | x | x | | | | x | x | x |
| Tami Flu | | 2006 Feb. 8 | o | o | x | | | | x | o | x |
| Nexia | 12 months | 2007 Feb. 23 | x | x | x | | | | x | x | x |

Further, point mutation in gene such as V599E of BRAF was repaired to V599V by LTN treatment (see Table 7).

TABLE 7

| | | | Mutation | | |
|---|---|---|---|---|---|
| Medication | Tx period | Exam Date | p53 | K-RAS | BRAF |
| none | | 2005 Jan. 27 | x | x | V599E |
| Nexia | 7 months | 2005 Sep. 7 | x | x | x |
| Tami Flu | | 2006 Feb. 8 | o | x | x |
| Nexia | 12 months | 2007 Feb. 23 | o | x | x |

In addition, by the treatment of the luterion, overexpressed Her-2/Neu gene was downregulated (see Table 8).

TABLE 8

| | | | Overexpression | | | | | | |
|---|---|---|---|---|---|---|---|---|---|
| Medication | Tx period | Exam Date | Cytokeratin7 | MAGE-A1 | MAGE-A3/6 | PSA | PSMA | Her-2/Neu | mucin-1 |
| none | | 2005 Jan. 27 | x | x | | | | o | |
| Nexia | 7 months | 2005 Sep. 7 | x | x | | | | x | |
| Tami Flu | | 2006 Feb. 8 | x | x | | | | x | |
| Nexia | 12 months | 2007 Feb. 23 | o | x | | | | o | |

| | | | Overexpression | | | | | |
|---|---|---|---|---|---|---|---|---|
| Medication | Tx period | Exam Date | mucin-6 | mucin-16 | RET_TK exon 15-16 | CA19-9 | CA125 | PSA |
| none | | 2005 Jan. 27 | | | x | | | |
| Nexia | 7 months | 2005 Sep. 7 | | | x | | | |
| Tami Flu | | 2006 Feb. 8 | | | o | | | |
| Nexia | 12 months | 2007 Feb. 23 | | | o | | | |

INDUSTRIAL APPLICABILITY

The composition comprising the luterion according to the present disclosure inhibits telomerase activity in cancer cells and has no effect on normal cells or promotes telomerase activity in normal cells. Thus, the composition effectively inhibits proliferation of only cancer cells to have anti-cancer effect.

As described above, the specific portions of the present disclosure are described in detail. It will be apparent by those skilled in the art that such descriptions are for preferable embodiments, but the present disclosure is not limited thereto. Therefore, the substantial scope of the present disclosure will be defined by the appended claims and their equivalents.

The invention claimed is:

1. A method of inhibiting telomerase activity in a cancer tissue, cancer cell or cancer patient in need of such inhibiting, comprising administering a composition comprising a luterion as an active ingredient in an effective amount, wherein the luterion is obtained by a method comprising:
   (a) adding a solvent to a plant and shaking it while bubbling intermittently with air or oxygen;
   (b) collecting vapor or gas vaporized by the shaking and then cooling to obtain a condensate;
   (c) filtering the obtained condensate using a filter having pores of from 0.8 μm to 1.2 μm;
   (d) centrifuging the filtered condensate; and
   (e) irradiating a supernatant obtained through the centrifugation with IR light to isolate luterion gathered with motility.

2. The method according to claim 1, wherein the luterion is derived from a medicinal plant selected from the group consisting of Ganghwal (*Ostericum koreanum* Maximowicz), Dokhwal (*Aralia continentalis* Kitagawa), Hyeonggae (*Schizonepeta tenuifolia* Briquet), Bangpung (*Saposhnikovia divaricata* Schischkin), Saengjihwang (*Rehmannia glutinosa* Liboschitz ex Steudel), bongnyeong (*Poria cocos* Wolf), Jeonho (*Angelica decursiva* Franchet et Savatier), Chajeonja (jilkyungee: *Plantago asiatica* Linne), Jigolpi (gugija: *Lycium chinense* Miller), Siho (*Bupleurum falcatum* Linne), Taeksa (*Alisma orientale* Juzepzuk), Moktong (*Akebia quinata* Decaisne), Hyeonsam (*Scrophularia ningpoensis* Hemsley), Gwalluin (*Trichosanthes kirilowii* Maximowicz), Jeoryeong (*Polyporus umbellatus* Fries), Hwangnyeon (*Coptis japonica* Makino), Gosam (*Sophora flavescens* Solander ex Aiton), Hwangbaek (*Phellodendron amurense* Ruprecht), Jimo (*Anemarrhena asphodeloides* Bunge), Sukjihwang (*Rehmannia glutinosa* Liboschitz ex Steudel), Sansuyu (*Cornus officinalis* Siebold et Zuccarini), Mokdanpi (*Paeonia suffruticosa* Andrews), Bokbunj a (*Rubus coreanus* Miguel), Indongdeung (*Lonicera japonica* Thunberg), Bakha (*Mentha arvensis* Linne var. *piperascens* Malinvaud ex Holmes), Chija (*Gardenia jasminoides* Ellis), Yeongyo (*Forsythia viridissima* Lindley), Ubangj a (*Arctium lappa Linne), MihuDeung (Darae: *Actinidia arguta* PLANCH), Mihudo (*Actinidia arguta* Fructus), mokgwa (*Chaenomelis* Fructus), Podogeun (*Vitis vinifera* Radix), Nogeun (*Phragmitis* Rhizoma), Aengdo (*Prunus tomentosa* Thunb), Ogapi (*Acanthopanax sessiliflorum* SEEM), Songhwabun (*Pinus densiflora* S. et Z), Jeodugangbansi (rice bran on a mallet head), Cheongsongjeol (*Pinus tabulaeformis*), Gyomaekmi (*Semen Fagopyri*), Sumac (*Rhus verniciflua*), Cheongung (*Cnidium officinale* Makino), Danggwi (*Angelica Gigas* Nakai), Jinpi (*Citri Unshius* Pericarpium), Jeokhasuo (*Polygonum multiflorum* Thunberg), Baeksuo (*Cynanchum wilfordii* Hemsley), Ginseng (*Panax ginseng* C. A. Meyer), Baekchul (*Atractylodes japonica* Koidzumi), Changchul (*Atractylodes lancea* De Candlle), Geongang (ginger: *Zingiber officinale* Roscoe), Yukgye (cinnamon: *Cinnamomum cassia* Presl), Cheongpi (mandarin tree: *Citrus unshiu* Markovich), Gwakhyang (*Agastache rugosa* O. Kuntze), Jasoyeop (*Perilla frutescens* Britton var. *acuta* Kudo), jujube (*Zizyphus jujuba* Miller var. *inermis* Rehder), Gamcho (*Glycyrrhiza uralensis* Fischer), Buja (*Aconitum carmichaeli* Debeaux), Hyangbuja (*Cyperus rotundus* Linne), Hwanggi (*Astragalus membranaceus* Bunge), Baekjagyak (*Paeonia lactiflora* Pallas), Sohoehyang (*Foeniculum vulgare* Miller), Goryanggang (*Alpinia officinarum* Hance), Daebokpi (*Areca catechu* Linne), Banha (*Pinellia ternata* Breitenbach), Namseong (*Arisaema amurense* Maximowicz var. *serratum* Nakai), Ikji (*Alpinia oxyphylla* Miguel), Jisil (trifoliate orange: *Poncirus trifoliata* Rafinesque), Hubak (*Magnolia ovobata* Thunberg), Mokhyang (*Aucklandia lappa* Decne), Osuyu (*Evodiae rutaecarpa* Bentham), Pagoji (*Psoralea corylifolia* Linn), Chongbaek (Root of green onion: *Allium fistulosum* Linn), Sain (*Amomum villosum* Loureiro), Sansa (*Crataegus pinnatifida* Bunge), Mahwang (*Ephedra sinica* Staph), Gamguk (*chrysanthemum indicum* Linne), Gilgyeong (balloon flower: *Platycodon grandiflorum*), Haengin (apricot tree: *Prunus armeniaca* var. ansu Max.), Baekji (*Angelica dahurica* BENTH. et HOOK), Maengmundong (*Liriope muscari* BALL), Cheonmundong (*Asparagus cochinchinensis* Merr), Sanyak (Chinese Yam:*Dioscorea japonica* THUNB), Sanjoin (*Zizyphus jujube*), Yongannyuk (*Dimocarpus longan* Lour), Wonji (*Polygala tenuifolia*), Seokchangpo (*Acorus graminens* SOLAND), Omija (*Schizandra chinensis* BAALL), Geonyul (*Castanea crenata* S. et Z.), Uiiin (*Coix lachryma-jobi* var. ma-yuen), Nabokja (daikon: *Raphanus sativus* L), Galgeun (kudzu: *Pueraria thunbergiana*), Hwanggeum (*Scutellaria baicalensis* GEORG), Gobon (*Angelica tenuissima* NAKAI), Nogyong (*Cervi Parvum* Cornu), Daehwang (*Rheum palmatum*), Seungma (*Cimicifuga heracleifolia* KOM), Baekjain (*Biota orientalis* ENDL), Sangbaekpi (mulberry: *Morus alba* L), Gwandonghwa (*Tussilago* farfara), Baekgwa (*Gingko biloba* L), Sahyangpul (*Thymus* vularis) and Jogak (*Gleditsia japonica* Miguel var. *koraiensis* Nakai).

3. The method according to claim 2, wherein the medicinal plant is Sumac (*Rhus verniciflua* stokes).

4. The method according to claim 1, wherein the luterion up-regulates expression of Sirt1 or p53 gene in cancer cells.

5. The method according to claim 1, wherein the luterion down-regulates mTOR gene expression in cancer cells.

6. The method according to claim 1, wherein the luterion
   i) demethylates a promoter selected from the group consisting of RAR-beta-2, APC, DAP-K, MGMT, GST-P1 and ppENK,
   ii) repairs point mutation in genes of which expression causes a cancer, and
   iii) downregulates the overexpressed genes of which expression causes a cancer.

7. The method according to claim 1, wherein the cancer is a lung cancer cell, a pancreatic cancer, a breast cancer or a colon cancer.

* * * * *

UNITED STATES PATENT AND TRADEMARK OFFICE
CERTIFICATE OF CORRECTION

PATENT NO. : 10,406,188 B1
APPLICATION NO. : 15/641947
DATED : September 10, 2019
INVENTOR(S) : Young Ah Kwon Page 1 of 1

It is certified that error appears in the above-identified patent and that said Letters Patent is hereby corrected as shown below:

In the Specification

Column 7, Table 1, Line 65: "Miguel" should read -- Miquel --.

Column 8, Table 3, Line 58: "Miguel" should read -- Miquel --.

Column 9, Table 4, Line 30: "Miguel" should read -- Miquel --.

Column 12, Line 31: "600 inn" should read -- 600 μm --.

In the Claims

Column 16, Line 63 Claim 2: "Bokbunj a" should read -- Bokbunja --.

Column 16, Line 64 Claim 2: "Miguel" should read -- Miquel --.

Column 16, Line 67 Claim 2: "Ubangj a" should read -- Ubangja --.

Column 17, Line 28 Claim 2: "Miguel" should read -- Miquel --.

Column 18, Line 18 Claim 2: "Miguel" should read -- Miquel --.

Signed and Sealed this
Twenty-second Day of October, 2019

Andrei Iancu
*Director of the United States Patent and Trademark Office*